(12) United States Patent
Baker, Jr. et al.

(10) Patent No.: US 8,109,272 B2
(45) Date of Patent: Feb. 7, 2012

(54) CARBON DIOXIDE-SENSING AIRWAY PRODUCTS AND TECHNIQUE FOR USING THE SAME

(75) Inventors: Clark R. Baker, Jr., Newman, CA (US); Roger Mecca, Danville, CA (US); Michael P. O'Neil, Pleasanton, CA (US); Rafael Ostrowski, Pittsburg, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1359 days.

(21) Appl. No.: 11/526,861

(22) Filed: Sep. 25, 2006

(65) Prior Publication Data
US 2008/0072913 A1  Mar. 27, 2008

(51) Int. Cl.
*A61M 16/04* (2006.01)
(52) U.S. Cl. .............................. 128/207.14; 128/204.23
(58) Field of Classification Search ............. 128/200.24, 128/200.26, 204.22, 204.23, 205.19, 207.14–207.18; 73/23.2, 23.22
See application file for complete search history.

(56) References Cited

U.S. PATENT DOCUMENTS

| | | | |
|---|---|---|---|
| 2,136,236 A | 11/1938 | Draper |
| 2,638,096 A | 5/1953 | Waldhaus |
| 2,880,072 A | 3/1959 | Grosskopf |
| 2,890,177 A | 6/1959 | Kilmer |
| 2,904,033 A | 9/1959 | Shane |
| 3,067,015 A | 12/1962 | Lawdermilt |
| 3,068,073 A | 12/1962 | Stanford |
| 3,113,842 A | 12/1963 | Udall |
| 3,114,610 A | 12/1963 | Gafford et al. |
| 3,238,020 A | 3/1966 | Eiseman |
| 3,363,833 A | 1/1968 | Laerdal |
| 3,373,735 A | 3/1968 | Gallagher |
| 3,420,635 A | 1/1969 | Davis |
| 3,467,601 A | 9/1969 | Brauer |
| 3,505,022 A | 4/1970 | Luckey |
| 3,507,623 A | 4/1970 | McConnaughey |
| 3,556,122 A | 1/1971 | Laerdal |
| 3,612,048 A | 10/1971 | Takaoka et al. |
| 3,615,233 A | 10/1971 | Doering et al. |
| 3,659,586 A | 5/1972 | Johns et al. |
| 3,694,164 A | 9/1972 | Guenther |
| 3,754,867 A | 8/1973 | Guenther |
| 3,830,630 A | 8/1974 | Kiefer et al. |

(Continued)

FOREIGN PATENT DOCUMENTS
DE  1 007 525  5/1957

(Continued)

OTHER PUBLICATIONS

International Search Report, PCT/US2007/020619, 6 pages, mailed Jun. 4, 2008.

(Continued)

*Primary Examiner* — Justine Yu
*Assistant Examiner* — Latoya M Louis
(74) *Attorney, Agent, or Firm* — Fletcher Yoder

(57) ABSTRACT

An airway device is provided that may track the flow of respiratory gases through the device with sensing elements at a plurality of locations along the gas flow path of the device. Such a device may be useful for assessing a variety of clinical states, for adjusting patient ventilator settings, or for determining whether or not an airway device has been properly inserted into a patient airway.

42 Claims, 8 Drawing Sheets

U.S. PATENT DOCUMENTS

| | | | |
|---|---|---|---|
| 3,931,822 A | 1/1976 | Marici | |
| 4,003,709 A | 1/1977 | Eaton et al. | |
| 4,019,862 A | 4/1977 | Dahms | |
| 4,077,404 A | 3/1978 | Elam | |
| 4,106,502 A | 8/1978 | Wilson | |
| 4,144,306 A | 3/1979 | Figueras | |
| 4,277,251 A | 7/1981 | Leichnitz | |
| 4,287,153 A | 9/1981 | Towsend | |
| 4,332,771 A | 6/1982 | Leichnitz | |
| 4,346,584 A | 8/1982 | Boehringer | |
| 4,366,821 A | 1/1983 | Wittmaier et al. | |
| 4,389,372 A | 6/1983 | Lalin | |
| 4,438,067 A | 3/1984 | Siddiqi | |
| 4,548,906 A | 10/1985 | Sekikawa et al. | |
| 4,557,900 A | 12/1985 | Heitzmann | |
| 4,557,901 A | 12/1985 | Koyama et al. | |
| 4,691,701 A | 9/1987 | Williams | |
| 4,728,499 A | 3/1988 | Fehder | |
| 4,734,125 A | 3/1988 | Gehring et al. | |
| 4,749,358 A | 5/1988 | Good et al. | |
| 4,774,941 A | 10/1988 | Cook | |
| 4,780,411 A | 10/1988 | Piejko et al. | |
| 4,788,153 A | 11/1988 | Detwiler et al. | |
| 4,790,327 A | 12/1988 | Despotis | |
| 4,824,640 A | 4/1989 | Hildenbrand et al. | |
| 4,879,999 A | 11/1989 | Leiman et al. | |
| 4,886,059 A | 12/1989 | Weber | |
| 4,928,687 A | 5/1990 | Lampotang et al. | |
| 4,945,918 A | 8/1990 | Abernathy | |
| 4,994,117 A | 2/1991 | Fehder | |
| 4,999,306 A | 3/1991 | Yafuso et al. | |
| 5,005,572 A | 4/1991 | Raemer et al. | |
| 5,076,268 A | 12/1991 | Weber | |
| 5,109,840 A | 5/1992 | Daleiden | |
| 5,124,129 A | 6/1992 | Riccitelli et al. | |
| 5,156,159 A | 10/1992 | Lampotang et al. | |
| 5,166,075 A | 11/1992 | Fehder | |
| 5,179,002 A | 1/1993 | Fehder | |
| 5,197,464 A | 3/1993 | Babb et al. | |
| 5,279,289 A | 1/1994 | Kirk | |
| 5,291,879 A | 3/1994 | Babb et al. | |
| 5,322,612 A | 6/1994 | Abe et al. | |
| 5,361,753 A | 11/1994 | Pothmann et al. | |
| 5,375,592 A | 12/1994 | Kirk et al. | |
| 5,445,144 A | 8/1995 | Wodicka et al. | |
| 5,456,249 A | 10/1995 | Kirk | |
| 5,468,451 A | 11/1995 | Gedeon | |
| 5,472,668 A | 12/1995 | Mills et al. | |
| 5,480,611 A | 1/1996 | Mills et al. | |
| 5,517,985 A | 5/1996 | Kirk et al. | |
| 5,520,997 A | 5/1996 | Pourahmady et al. | |
| 5,634,426 A | 6/1997 | Tomlinson et al. | |
| 5,679,884 A | 10/1997 | Kirk | |
| 5,714,121 A | 2/1998 | Alderete et al. | |
| 5,752,921 A | 5/1998 | Orr | |
| 5,783,110 A | 7/1998 | Verdicchio et al. | |
| 5,785,051 A | 7/1998 | Lipscher et al. | |
| 5,846,836 A | 12/1998 | Mallow | |
| 5,849,594 A | 12/1998 | Balderson et al. | |
| 6,000,397 A | 12/1999 | Skog | |
| 6,055,447 A | 4/2000 | Weil et al. | |
| 6,058,933 A | 5/2000 | Good et al. | |
| 6,071,237 A * | 6/2000 | Weil et al. | 600/309 |
| 6,123,075 A | 9/2000 | Kirk | |
| 6,216,024 B1 | 4/2001 | Weil et al. | |
| 6,265,221 B1 | 7/2001 | Nilsson | |
| 6,319,723 B1 | 11/2001 | Jeffers et al. | |
| 6,349,720 B1 | 2/2002 | Clark | |
| 6,378,522 B1 | 4/2002 | Pagan | |
| 6,397,846 B1 | 6/2002 | Skog | |
| 6,427,687 B1 | 8/2002 | Kirk | |
| 6,428,748 B1 | 8/2002 | Wallach | |
| 6,436,347 B1 | 8/2002 | Cedeon | |
| 6,502,573 B1 | 1/2003 | Ratner | |
| 6,576,474 B2 | 6/2003 | Wallach | |
| D478,522 S | 8/2003 | Geist | |
| 6,677,159 B1 | 1/2004 | Mallow | |
| 6,709,403 B1 | 3/2004 | Ratner | |
| 6,929,008 B2 | 8/2005 | Geist | |
| 6,961,600 B2 | 11/2005 | Kohl et al. | |
| 7,017,578 B2 | 3/2006 | Tresnak et al. | |
| 7,140,370 B2 | 11/2006 | Tresnak et al. | |
| 7,273,050 B2 | 9/2007 | Wei | |
| 2003/0003593 A1 | 1/2003 | Wallach | |
| 2003/0133123 A1 | 7/2003 | Yeh | |
| 2003/0199095 A1 | 10/2003 | Yuyama et al. | |
| 2004/0065329 A1 | 4/2004 | Geist | |
| 2004/0123867 A1 | 7/2004 | Efrati | |
| 2004/0184024 A1 | 9/2004 | Katura et al. | |
| 2005/0016543 A1 | 1/2005 | Geist | |
| 2005/0039751 A1 | 2/2005 | Pagan | |
| 2005/0235998 A1 | 10/2005 | Tresnak et al. | |
| 2005/0279360 A1 | 12/2005 | Wei | |
| 2006/0091010 A1* | 5/2006 | Komatsu et al. | 204/427 |
| 2006/0201503 A1 | 9/2006 | Breen | |
| 2007/0048181 A1* | 3/2007 | Chang et al. | 422/57 |
| 2007/0062540 A1* | 3/2007 | Murray-Harris | 128/207.29 |
| 2007/0107737 A1 | 5/2007 | Landis et al. | |
| 2007/0134156 A1* | 6/2007 | Laitenberger et al. | 435/7.1 |
| 2007/0137651 A1* | 6/2007 | Glassenberg et al. | 128/207.15 |
| 2008/0210235 A1 | 9/2008 | Field et al. | |
| 2009/0038620 A1 | 2/2009 | Efrati | |
| 2009/0229605 A1* | 9/2009 | Efrati et al. | 128/203.12 |

FOREIGN PATENT DOCUMENTS

| | | |
|---|---|---|
| DE | 10222176 A1 | 11/2003 |
| EP | 0 481 719 A1 | 4/1992 |
| EP | 0 307 625 B1 | 4/1994 |
| EP | 0 257 916 A1 | 1/1995 |
| EP | 0 509 998 B1 | 1/1996 |
| EP | 0 451 719 B1 | 12/1996 |
| EP | 0 601 171 B1 | 9/1997 |
| EP | 0 592 632 B1 | 8/1999 |
| EP | 01 022 558 A2 | 7/2000 |
| EP | 1 022 558 A3 | 7/2000 |
| EP | 1 039 294 A2 | 9/2000 |
| EP | 1 039 294 A3 | 10/2000 |
| EP | 1 245 947 A1 | 10/2002 |
| EP | 1 266 944 A1 | 12/2002 |
| EP | 0 858 594 B1 | 4/2003 |
| EP | 1 327 874 A2 | 7/2003 |
| EP | 1 153 294 B1 | 10/2003 |
| EP | 0 943 093 B1 | 11/2003 |
| GB | 1 043 988 A | 9/1966 |
| JP | 07072081 A | 3/1995 |
| JP | 08145979 A | 6/1996 |
| JP | 08247997 A | 9/1996 |
| JP | 09318528 A | 12/1997 |
| JP | 10073560 A | 3/1998 |
| JP | 2003072857 A | 3/2003 |
| JP | 2004177247 A | 6/2004 |
| JP | 2005054048 A | 3/2005 |
| WO | WO 90/01695 A1 | 2/1990 |
| WO | WO 90/03819 A1 | 4/1990 |
| WO | WO 91/05252 A1 | 4/1991 |
| WO | WO 92/20404 A1 | 11/1992 |
| WO | WO 93/20431 A1 | 10/1993 |
| WO | WO 94/00756 A1 | 1/1994 |
| WO | WO 96/19727 A1 | 6/1996 |
| WO | WO 96/24054 A1 | 8/1996 |
| WO | WO 97/10496 A1 | 3/1997 |
| WO | WO 97/12227 A1 | 4/1997 |
| WO | WO 98/26283 A1 | 6/1998 |
| WO | WO 00/29830 A1 | 5/2000 |
| WO | WO 00/43778 A1 | 7/2000 |
| WO | WO 01/04624 A1 | 1/2001 |
| WO | WO 01/44385 A1 | 6/2001 |
| WO | WO 01/56454 A2 | 8/2001 |
| WO | WO 2003/045608 A1 | 3/2003 |
| WO | WO 2004/077035 A1 | 9/2004 |

OTHER PUBLICATIONS

J.A. Berman et al.; "The Einstein Carbon Dioxide Detector"; Anesthesiology, vol. 60, No. 6; pp. 613-614 (1984).

P.K. Birmingham et al.; "Esophageal Intubation: A Review of Detection Techniques"; Anesth. Analg.; vol. 65; pp. 886-891 (1986).

Butler et al., "Combined Use of the Esophageal-Tracheal Combitube with a Colorimetric Carbon Dioxide Detect for Emergency Intubation/Ventilation," Clinical Monitoring, vol. 11, No. 5, Sep. 1995, pp. 311-316.

Cardoso, Monica M. S. C. MD et al., Portable Devices Used to Detect Endotracheal Intubation During Emergency Situations: A Review, Critical Care Medicine, May 1998, pp. 957-964, vol. 26, Issue 5.

Gravenstein, D. et al., Breakthroughs in Endotracheal Tube Design and Verification of Tracheal Placement, University of Florida, Office of Technology Licensing, pp. 1-2.

Sheridan ETCO2 Uncuffed Endotracheal Tubes, Monitoring Lumen Tubes, Hudson RCI, 2010, pp. 1-2.

International Search Report PCT/US2007/020587, 4 pages, mailed Jun. 2, 2008.

* cited by examiner

CARBON DIOXIDE-SENSING AIRWAY PRODUCTS AND TECHNIQUE FOR USING THE SAME

BACKGROUND OF THE INVENTION

1. Field of the Invention

The present invention relates generally to medical devices and, more particularly, to patient ventilation devices, such as breathing circuits and tracheal tubes.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

Physiological characteristics that physicians may desire to monitor include constituents of the blood and tissue, such as oxygen and carbon dioxide. For example, abnormal levels of carbon dioxide in the blood or tissue may be related to poor perfusion. Thus, assessment of carbon dioxide levels may be useful for diagnosing a variety of clinical states related to poor perfusion. Carbon dioxide and other blood constituents may be directly measured by taking a blood sample, or may be indirectly measured by assessing the concentration of those constituents in the tissue or respiratory gases. For example, carbon dioxide in the bloodstream equilibrates rapidly with carbon dioxide in the lungs, and the partial pressure of the carbon dioxide in the lungs approaches the amount in the blood during each breath. Accordingly, physicians often monitor respiratory gases during breathing in order to estimate the carbon dioxide levels in the blood.

In the course of treating a patient, a tube or other medical device may be used to control the flow of air, food, fluids, or other substances into the patient. For example, medical devices, such as tracheal tubes, may be used to control the flow of one or more substances into or out of a patient. Such tracheal tubes may include endotracheal (ET) tubes or tracheostomy tubes. In this way, substances can only flow through the passage via the tube or other medical device, allowing a medical practitioner to maintain control over the type and amount of substances flowing into and out of the patient. Such airway devices may be part of a breathing circuit that allows a physician to facilitate mechanical ventilation of the patient.

In certain instances, it may be advantageous to assess carbon dioxide in respiratory gases that are flowing through airway devices. The carbon dioxide levels in such gases are generally less contaminated by environmental gases because the airway devices provide at least a partial barrier to the egress or ingress of gas. Further, such information is useful to a healthcare practitioner to determine whether the airway device is transferring sufficient respiratory gas to the lungs or to determine whether the patient is metabolizing the respiratory gas and producing the expected levels of carbon dioxide or other volatile metabolites. Thus, sampling carbon dioxide in an airway device may provide a useful method of assessing physiological carbon dioxide levels.

SUMMARY

Certain aspects commensurate in scope with the originally claimed invention are set forth below. It should be understood that these aspects are presented merely to provide the reader with a brief summary of certain forms that the invention might take, and that these aspects are not intended to limit the scope of the invention. Indeed, the invention may encompass a variety of aspects that may not be set forth below.

There is provided a medical device that includes a conduit adapted to transfer a gas to or from a patient; and a plurality of sensing components associated with a respective plurality of locations on the conduit, wherein the plurality of sensing components is adapted to provide a signal related to a carbon dioxide gas in the conduit at the respective plurality of locations.

There is provided a system that includes a conduit adapted to transfer a gas to or from a patient; a plurality of sensing components associated with a respective plurality of locations on the conduit, wherein the plurality of sensing components is adapted to provide a signal related to a carbon dioxide gas in the conduit at the respective plurality of locations; and a monitor adapted to be operatively coupled to the plurality of sensing components.

There is provided a method of manufacturing a medical device that includes providing a conduit adapted to transfer a gas to or from a patient; and providing a plurality of sensing components associated with a respective plurality of locations on the conduit, wherein the plurality of sensing components is adapted to provide a signal related to a carbon dioxide gas in the conduit at the respective plurality of locations.

There is provided a medical device that includes: a conduit adapted to transfer a gas to or from a patient; and a contiguous sensing component disposed along at least a portion of the conduit, wherein the contiguous sensing component is adapted to provide an indication of a carbon dioxide gas in the conduit along the portion of the conduit.

There is provided a system that includes a conduit adapted to transfer a gas to or from a patient; and a contiguous sensing component disposed along at least a portion of the conduit, wherein the contiguous sensing component is adapted to provide an indication of a carbon dioxide gas in the conduit along the portion of the conduit; and a monitor adapted to be operatively coupled to the contiguous sensing element at each of the plurality of locations.

There is provided a method of manufacturing a medical device that includes providing a conduit adapted to transfer a gas to or from a patient; and a contiguous sensing component disposed along at least a portion of the conduit, wherein the contiguous sensing component is adapted to provide an indication of a carbon dioxide gas in the conduit along the portion of the conduit.

There is provided a medical system adapted to determine a change in a non-gas-exchanging physiologic volume in a ventilated patient that includes a processor adapted to: receive signals from a plurality of carbon dioxide sensors disposed on a patient breathing circuit; determine a concentration of carbon dioxide gas over time at a first location in a patient breathing circuit; determine a concentration of carbon dioxide gas over time at a second location in the patient breathing circuit; determine the transit time of the carbon dioxide gas between the two locations; determine the volume of the breathing circuit between the first and second locations based on the cross-sectional area of the breathing circuit and the distance between the two locations; and determine the flow rate over time of the carbon dioxide gas between the first location and the second location in the patient breathing circuit based on the determined volume and transit time, wherein a change in non-gas-exchanging physiologic volume is indicated by a change in the total volume exhaled while the carbon dioxide gas is increasing at the start of exhalation.

There is also provided a computer readable medium with instructions for determining a change in a non-gas-exchanging physiologic volume in a ventilated patient that includes: code for receiving signals from a plurality of carbon dioxide sensors disposed on a patient breathing circuit; code for determining a concentration of carbon dioxide gas over time at a first location in a patient breathing circuit; code for determining a concentration of carbon dioxide gas over time at a second location in the patient breathing circuit; code for determining the transit time of the carbon dioxide gas between the two locations; code for determining the volume of the breathing circuit between the first and second locations based on the cross-sectional area of the breathing circuit and the distance between the two locations; and code for determining the flow rate over time of the carbon dioxide gas between the first location and the second location in the patient breathing circuit based on the determined volume and transit time, wherein a change in non-gas-exchanging physiologic volume is indicated by a change in the total volume exhaled while the carbon dioxide gas is increasing at the start of exhalation.

There is also provided a method of determining a change in a non-gas-exchanging physiologic volume in a ventilated patient that includes: determining a concentration of carbon dioxide gas over time at a first location in a patient breathing circuit; determining a concentration of carbon dioxide gas over time at a second location in the patient breathing circuit; determining the transit time of the carbon dioxide gas between the two locations; determining the volume of the breathing circuit between the first and second locations based on the cross-sectional area of the breathing circuit and the distance between the two locations; and determining the flow rate over time of the carbon dioxide gas between the first location and the second location in the patient breathing circuit based on the determined volume and transit time, wherein a change in non-gas-exchanging physiologic volume is indicated by a change in the total volume exhaled while the carbon dioxide gas is increasing at the start of exhalation.

There is provided a multi-lumen intubation tube that includes a conduit adapted to transfer gas to a patient's lungs that includes a first lumen and a second lumen; a first carbon dioxide sensing component disposed on the first lumen; and a second carbon dioxide sensing component disposed on the second lumen.

There is also provided a method of manufacturing a multi-lumen intubation tube that includes: providing a conduit adapted to transfer gas to a patient's lungs comprising a first lumen and a second lumen; providing a first carbon dioxide sensing component disposed on the first lumen; and providing a second carbon dioxide sensing component disposed on the second lumen.

There is provided a method of determining which lumen is active in a multi-lumen tube that includes inserting a multi-lumen tube into a patient's airway; determining a concentration of carbon dioxide gas at a location in a first lumen; and determining a concentration of carbon dioxide gas at a location in a second lumen, wherein the lumen with the higher concentration of carbon dioxide gas is the active lumen.

There is also provided a system that includes: a conduit adapted to transfer gas to or from a patient's lungs; an inflatable balloon cuff disposed on the conduit; and at least one carbon dioxide sensing component disposed on the inflatable balloon cuff; and a monitor adapted to be operatively coupled to the plurality of sensing components.

There is also provided a method of manufacturing a medical device that includes: providing a conduit adapted to transfer a gas to or from a patient; providing an inflatable balloon cuff disposed on the conduit; and providing at least one carbon dioxide sensing component disposed on the inflatable balloon cuff.

There is also provided a method that includes: receiving a signal from at least one carbon dioxide sensing component disposed on an inflatable balloon cuff operatively connected to an endotracheal tube; and correlating the signal to a level of secretions on the cuff.

There is also provided a method that includes: receiving a first signal from a first carbon dioxide sensing component disposed on an endotracheal tube; receiving a second signal from a second carbon dioxide sensing component disposed on an endotracheal tube; and correlating a difference between the first signal and the second signal to a level of secretions on a surface of the endotracheal tube.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is desirable to provide an airway device, such as an endotracheal tube or other medical device, which may sense carbon dioxide concentration at multiple points along the device. Having a plurality of carbon dioxide sensing components allows carbon dioxide concentrations to be tracked throughout a single breathing cycle as respiratory gases travel through the device and encounter each sensing component. This may allow more rapid monitoring of changes to carbon dioxide concentrations than typical devices that rely upon a single carbon dioxide sensor and track the carbon dioxide at a single point in each breathing cycle. Rapid monitoring of carbon dioxide concentration changes may provide certain advantages, such as more rapid detection of clinical states that may be related to the underlying carbon dioxide concentration changes. Further, providing carbon dioxide sensing components along the path of a patient airway device may allow a rapid visual signal that carbon dioxide in expired gases is flowing through the airway as expected. Alternatively, the lack of such a visual signal may direct immediate attention to leaky airway connections, non-optimal ventilator settings, or a change in the physiological state of the patient.

In certain embodiments, the present techniques may be used in conjunction with any appropriate medical device, including a feeding tube, an endotracheal tube, a tracheostomy tube, a circuit, an airway accessory, a connector, an adapter, a filter, a humidifier, a nebulizer, nasal cannula, or a laryngeal mask. The present techniques may also be used to monitor any patient benefiting from mechanical ventilation. Further, the devices and techniques provided herein may be used to monitor a human patient, such as a trauma victim, an intubated patient, a patient with a tracheostomy, an anesthetized patient, a cardiac arrest victim, a patient suffering from airway obstruction, or a patient suffering from respiratory failure.

Figure 1:
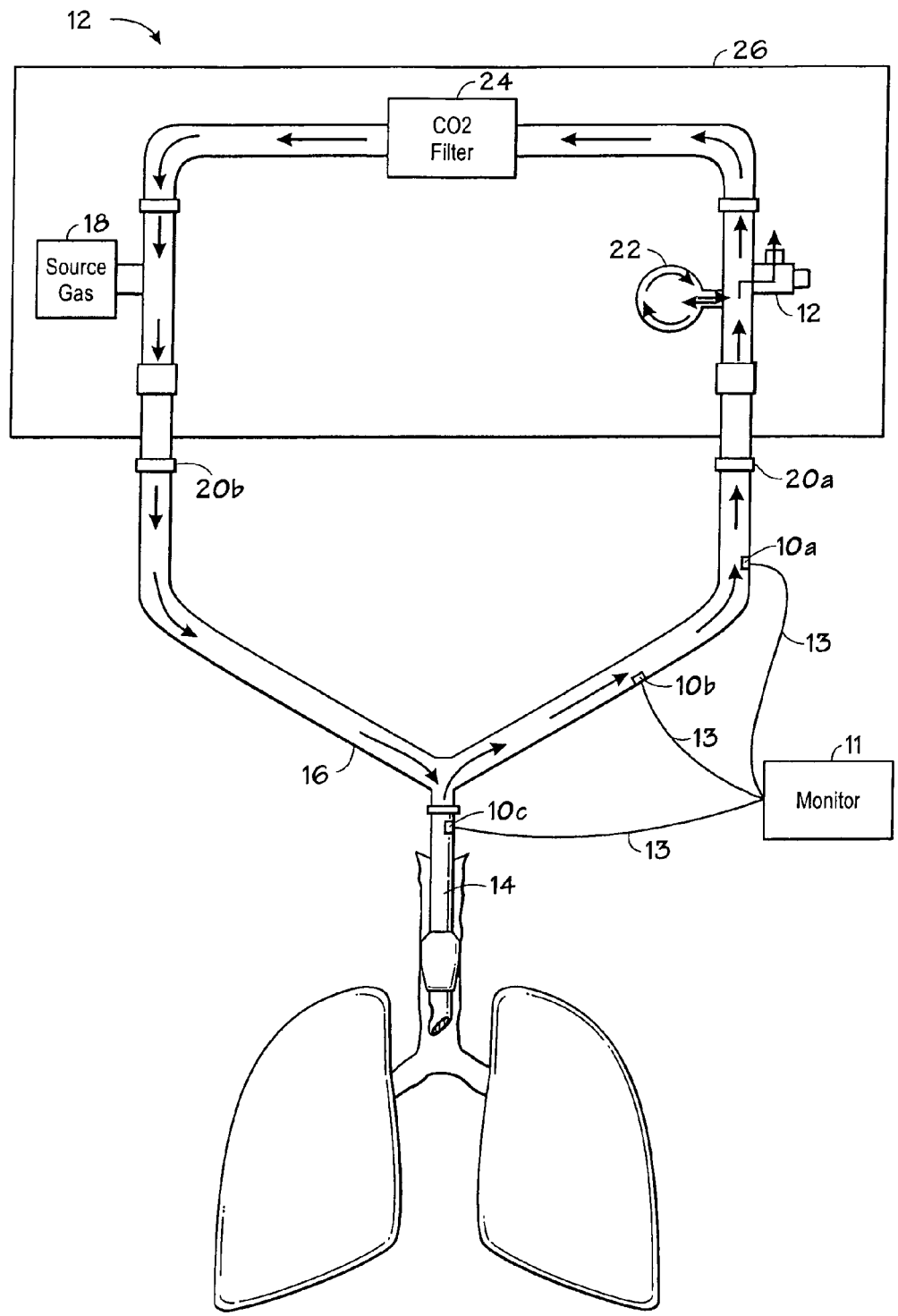
FIG. 1 illustrates an exemplary patient breathing circuit with multiple carbon dioxide sensing components in accordance with aspects of the present technique.

FIG. 1 illustrates a schematic of an exemplary patient breathing circuit 12 with multiple carbon dioxide sensing components 10a, 10b, and 10c, discussed in more detail herein. The sensing components, generically referred to by the reference numeral 10, may be used in conjunction with a carbon dioxide monitoring system 11. The sensing components 10 may be located along any point in the breathing circuit 12. For example, the sensing components may be located in the portion of the breathing circuit 12 inserted into the patient, or in any of the associated tubing or connectors. For example, in one embodiment, a sensing component 10 may be located directly after the carbon dioxide filter 24 in the airflow circuit in order to assess the quality of the carbon dioxide filter 24. In other embodiments, the sensing components 10 may be adapted to determine the level of carbon dioxide in an anesthetic gas mixture being delivered to the patient. It should be appreciated that the sensing components 10 may be coupled to the monitor 11 with cables 13 or may be coupled to a transmission device (not shown) to facilitate wireless transmission between the sensing components 10 and the monitor 11. The monitor 11 may be any suitable carbon dioxide monitor, such as those available from Nellcor Puritan Bennett Inc. Furthermore, to upgrade conventional carbon dioxide monitoring provided by the monitor 11 to provide additional functions, the monitor 11 may be coupled to a multi-parameter patient monitor (not shown).

The breathing circuit 12 may also include a Y-shaped respiratory circuit 16 that allows one-way flow of expired gases away from the patient and one-way flow of inspired gases from a source gas supply 18 towards the patient. The one-way flow of gases through the Y-shaped respiratory circuit 16 may be achieved through the use of inline one-way valves 20a and 20b. The source gas may include respiratory gas mixtures and anesthetic/therapeutic components such as anesthetic agents, nitric oxide, radioactively tagged particles and/or a variety of other gaseous agents. It will be appreciated that the expired gas stream may also include a combination of respiratory gases and anesthetic/therapeutic gases. The Y-shaped respiratory circuit 16 may also include a vent 21 and/or a gas reservoir 22 to relieve excess volume or pressure in the breathing circuit 12. The Y-shaped respiratory circuit 16 may also include a carbon dioxide filter 24 to remove carbon dioxide from breathing circuit 12 before the fresh source gas is added to the airflow.

The Y-shaped respiratory circuit 16 may be connected to the patient with any suitable airway device, such as a tracheal tube 14, as shown. The Y-shaped respiratory circuit 16 may include standard medical tubing made from suitable materials such as polyurethane, polyvinyl chloride (PVC), polyethylene teraphthalate (PETP), low-density polyethylene (LDPE), polypropylene, silicone, neoprene, or polyisoprene.

The breathing circuit 12 may be incorporated into systems that facilitate positive pressure ventilation of a patient, such as a ventilator 26. Such systems may typically include a monitor and/or a controller. The controller may be a digital controller, a computer, an electromechanical programmable controller, or any other control system. In certain embodiments (not shown), the breathing circuit 12 may include one or more temperature sensors that provide information to the monitor 11 about the temperature of gas flowing through the breathing circuit 12. Suitable temperature sensors according to the present techniques include any suitable medical grade temperature sensor, such as resistance-based temperature sensors and infrared temperature sensors available from Thermometrics (Plainville, Conn.). In other embodiments, the breathing circuit may include humidity and ambient pressure sensors. For example, in certain embodiments, it may be advantageous to determine spectral changes as a function of pressure. In such embodiments, a breathing circuit 12 may include barometric pressure sensors to determine ambient pressure or intra-circuit pressure.) In other embodiments, it may be advantageous for a healthcare worker to manually input ambient conditions, such as the temperature of room or the patient temperature, into the monitoring system.

As depicted, the endotracheal tube 28 may also include an inflatable cuff 34 that may be inflated to form a seal against the trachea walls. Typically, the cuff 34 is disposed, adhesively or otherwise, towards the distal end 36 of the conduit 32. The cuff 34 may be inflated and deflated via an inflation lumen 38 in communication with the cuff 34, typically through a hole or a notch in the conduit 32. The cuff 34 has a proximal opening 40 and a distal opening 42 formed in the cuff walls to accommodate the conduit 32. The cuff 34 may be formed from materials having suitable mechanical properties (such as puncture resistance, pin hole resistance, tensile strength), chemical properties (such as forming a suitable bond to the tube 32), and biocompatibility. In one embodiment, the walls of the inflatable cuff 34 are made of polyurethane having suitable mechanical and chemical properties. An example of a suitable polyurethane is Dow Pellethane® 2363-90A. In another embodiment, the walls of the inflatable cuff 34 are made of a suitable polyvinyl chloride (PVC).

Suitable materials may also include polyethylene teraphthalate (PETP), low-density polyethylene (LDPE), polypropylene, silicone, neoprene, or polyisoprene.

In addition to carbon dioxide monitoring, sensing components 10, as provided herein, may be used to monitor oxygen, carbon monoxide, volatile organic compounds such as ethanol, metabolic trace gases such as acetone, or anesthetic gases such as isoflurane, halothane, desflurane, sevoflurane, and enflurane. For example, respiratory gases associated with an acute or chronic disease state may be monitored using the present techniques.

In other embodiments (not shown), the sensing components 10 may be incorporated into systems that sense carbon dioxide transcutaneously. For example, in such a system, a gas chamber type collection system may be placed on a patient's skin to capture any gas that may diffuse away from the skin to a distal site. The carbon dioxide levels in the gas may be used as a surrogate marker for carbon dioxide levels in the blood, as blood carbon dioxide may diffuse through the tissue. The skin may be heated in order to facilitate the diffusion of gas through the tissue. The sensing components 10 may be located at multiple locations along the system and a change in the levels of carbon dioxide along the system may indicate a change in clinical state, such as poisoning.

Sensing components 10 as described herein may include any appropriate sensor or sensor element for assessing expired carbon dioxide, including chemical, electrical, optical, non-optical, quantum-restricted, electrochemical, enzymatic, spectrophotometric, fluorescent, or chemiluminescent indicators or transducers. In certain embodiments, the sensing component 10 may include optical components, e.g., an emitter and detector pair that may be of any suitable type. For example, the emitter may be one or more light emitting diodes adapted to transmit one or more wavelengths of light in the red to infrared range, and the detector may be one or more photodetectors selected to receive light in the range or ranges emitted from the emitter. Alternatively, an emitter may also be a laser diode or a vertical cavity surface emitting laser (VCSEL). An emitter and detector may also include optical fiber sensing components. An emitter may include a broadband or "white light" source, in which case the detector could include any of a variety of elements for selecting specific wavelengths, for example, reflective or refractive elements or interferometers. These kinds of emitters and/or detectors would typically be coupled to the rigid or rigidified sensor via fiber optics. Alternatively, a sensing component 10 may sense light detected through the respiratory gas at a different wavelength from the light emitted into the respiratory gas. Such sensors may be adapted to sense fluorescence, phosphorescence, Raman scattering, Rayleigh scattering and multi-photon events or photoacoustic effects. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the ultrasound, radio, microwave, millimeter wave, infrared, visible, ultraviolet, gamma ray or X-ray spectra.

The sensing component 10 may be an electrochemical transducer, which may be adapted to detect and measure changes in ambient chemical parameters induced by the presence of critical amounts of carbon dioxide. In one embodiment, the sensing component 10 may include a sensor that employs cyclic voltammetry for carbon dioxide detection. Such sensors are available from Giner, Inc., Newton, Mass. For example, the sensing component 10 may be a thick film catalyst sensor utilizing a proton exchange membrane. Such a sensing component 10 may include thick film screen printed electrodes and an electrochemically reversible metal oxide catalysts. Appropriate catalysts include $MO$, $M_2O_3$, $MO_2$, where M is a metal that is any suitable metal, including platinum, ruthenium, or iridium. Generally, such sensors operate by sensing chemical reactions caused by proton dissociation from water in which carbon dioxide is dissolved. Dissociated water protons may electrochemically reduce a metal oxide layer of the sensor. The electrochemical reduction of the metal oxide will result in generation of an electrical current, which varies in response to the degree of electrochemical reduction.

In another embodiment, the sensing component 10 may include quantum-restricted components, including carbon nanotubes, buckeyballs, or quantum dots. Generally, quantum-restricted components may be coated or otherwise modified with a compound that is sensitive to the respiratory gas of interest. Interaction of the respiratory gas with the compound may affect the electrical, optical, thermal, or physical properties of the quantum-restricted components such that a signal may result. In one such example, carbon nanotubes may be coated with a carbon dioxide-sensitive compound or polymer, such as a polyethyleneimine and starch polymer. Carbon dioxide may combine with primary and tertiary amines in the polyethyleneimine and starch polymer coating to form carbamates. The chemical reaction alters the charge transfer to the carbon nanotubes and results in an electrical signal. Other suitable polymer coatings may be adapted to sense other respiratory gases of interest, such as oxygen or carbon monoxide. In other embodiments, the quantum-restricted component may include a binding molecule, such as a receptor or an enzyme that is specific for the respiratory gas of interest. One such molecule may include carbonic anhydrase. Binding of the respiratory gas to its receptor may affect a downstream response that may result in a change in the electrical properties of a quantum-restricted component.

The sensing component 10 may also include a semi-conductive sensing element, such as a field-effect transistor (FET) or an ion-sensitive field-effect transistor (ISFET). An ISFET may include a silicon dioxide gate for a pH selective membrane. Such a sensor may be adapted to sense downstream changes in hydrogen ion concentration in response to changes in carbon dioxide or other respiratory gas concentrations. In certain embodiments, the semi-conductive sensing element may be a film.

Alternatively, the sensing component 10 may include an active ingredient of the indicating element, for example the active ingredient involved in providing the required response signal when exposed to a given concentration of carbon dioxide or other constituents. The active ingredient may be any indicator that is sensitive to the presence of carbon dioxide and that is capable of being calibrated to give a response signal corresponding to a given predetermined concentration of carbon dioxide. The signal may be visual, e.g., a change in color, or electrical. Indicators that provide a color change in a presence of carbon dioxide may include chromogenic pH-sensitive indicators and oxidation/reduction indicators.

A chromogenic pH-sensitive indicator may provide a color change upon exposure to a given concentration of carbon dioxide or other metabolites in the presence of other ingredients of the element that provide the appropriate chemical conditions to induce the required color change. For such an indicator to be capable of giving a determination of carbon dioxide, it is typically used in combination with a suitable base that provides an alkaline solution. The hydroxyl ions or amine residues present in the alkaline solution react chemically with carbon dioxide to produce a carbonate, bicarbonate and/or carbamate moiety. The resulting reaction depletes the hydroxyl ion or amine at the interface and thus lowers the pH at the surface of the component impregnated with the indicating element. The lowering of the pH causes a color change in the indicator.

Chromogenic pH-sensitive indicators, according to the present techniques, may include metacresol purple, thymol blue, cresol red, phenol red, xylenol blue, a 3:1 mixture of cresol red and thymol blue, bromthymol blue, neutral red, phenolphthalein, rosolic acid, alpha-naphtholphthalein and orange I. Examples of other indicators that may be used include bromcresol purple, bromphenol red, p-nitrophenol, m-nitrophenol, curcumin, quinoline blue, thymolphthalein and mixtures thereof. Suitable bases include sodium carbonate, lithium hydroxide, sodium hydroxide, potassium hydroxide, potassium carbonate, sodium barbitol, tribasic sodium phosphate, dibasic sodium phosphate, potassium acetate, monoethanolamine, diethanolamine and piperidine.

The sensing component 10 may also include an enzyme-based detection system. For example, one such enzyme may be carbonic anhydrase, which is an enzyme that assists interconversion of carbon dioxide and water into carbonic acid, protons, and bicarbonate ions. As described above, this reaction lowers the pH at the surface of the component impregnated with the indicating element. The lowering of the pH may cause a color change in the indicator. Another such enzyme-based detection system is an enzyme linked immunosorbent assay (ELISA). For example, such an assay may be appropriate when assessing tissue proteins. Thus, the indicator element may include a primary antibody specific for the tissue protein of interest, and a labeled secondary binding ligand or antibody, or a secondary binding ligand or antibody in conjunction with a labeled tertiary antibody or third binding ligand. The label may be an enzyme that will generate color development upon incubating with an appropriate chromogenic substrate. Suitable enzymes include urease, glucose oxidase, alkaline phosphatase or hydrogen peroxidase.

A chemical indicator may be used in conjunction with an electrical or electronic device that is adapted to detect and measure changes in the ambient chemical parameters induced by the presence of critical amounts of carbon dioxide. For example, optical fiber carbon dioxide sensing components 10 may be used to convert a change in a chemical indicator to a quantitative measurement of carbon dioxide in the sample. Generally, such sensing components 10 operate by directing light of a predetermined wavelength from an external source through the optical fiber to impinge the chemical indicator. The intensity of the emitted fluorescent light returning along the fiber is directly related to the concentration of carbon dioxide in the sample, as a result of the pH-sensitive indicator material present at the fiber tip (i.e., the pH of the indicator solution is directly related to carbon dioxide concentration, as a result of carbonic acid formation). The emitted light is carried by the optical fiber to a device where it is detected and converted electronically to a carbon dioxide concentration value. The sensing component 10 may additionally have a reference dye present in the indicator composition. The intensity of the light emitted from the reference dye may be used to compensate, via ratioing, the signal obtained from the indicator. Other components may be incorporated into the indicator composition including surfactants, antioxidants and ultraviolet stabilizers. The sensing component 10 may be formed from any appropriate substrate. For example, the sensing component 10 may be filter paper, which may be soaked in, dipped in, or otherwise exposed to the appropriate carbon dioxide-sensing compounds. In certain embodiments, the filter paper may be dipped into a solution containing the indicating compounds on only one side. The sensing component 10 may also be polysulfone, polypropylene, or other polymer substrates. The sensing component may be a thin film, or a thicker substrate. A thicker substrate may lead to a slower response time, which may be advantageous in situations in which a sensor is monitoring carbon dioxide levels over a longer period of time. Additionally, the sensing component may have pores of a variety of sizes.

In another embodiment, the sensing component 10 may include an artificial nose assembly. In such an embodiment, the respiratory gas may contact an array of electrodes coated with polymers that have characteristic electrical properties. For example, the polymers may change electrical resistance when contacted with specific materials.

In certain embodiments, the sensor sensing components 10 may include materials that function as a selective barrier that are hydrophobic or otherwise water-resistant, but are permeable to carbon dioxide or other respiratory gases. Such a barrier may be of some advantage in the humid environment of the breathing circuit 12. In one embodiment, it is envisioned that the ratio of water permeability to carbon dioxide permeability of a selective barrier may be less than 10, and, in certain embodiments, the ratio may be less than 1. Suitable materials for a selective barrier include polymers, such as polytetrafluoroethylene (PTFE). Other suitable materials include microporous polymer films, such as those available from the Landec Corporation (Menlo Park, Calif.). Such microporous polymer films are formed from a polymer film base with a customizable crystalline polymeric coating that may be customized to be highly permeable to carbon dioxide and relatively impermeable to water. The thickness of a selective barrier may be modified in order to achieve the desired rate of carbon dioxide perfusion and transducer response time. Generally, response times may be in the range of virtually instantaneous to less than 5 minutes. In certain embodiments, the response time is in the range of 5 seconds to 5 minutes. Where a very rapid response is desired, a thin film of the selective barrier, for example less than 0.2 mm in thickness, may be used. In certain embodiments, when a slower response is desired, a selective barrier may range from 0.2 mm to several millimeters in thickness. Additionally, the selective barrier may be formed with small pores that increase the carbon dioxide permeability. The pores may be of a size of 0.01 to approximately 10 microns, depending on the desired response time. In one embodiment, the selective barrier may be a relatively thin PTFE material such as plumber's tape (0.04 mm). In other embodiments, the selective barrier may be a PTFE material such as Gore-Tex® (W. L. Gore & Associates, Inc., Newark, Del.). Alternatively, the selective barrier 22 may be formed from a combination of appropriate materials, such as materials that are heat-sealed or laminated to one another. For example, the selective barrier may include a PTFE layer with a pore size of 3 microns and a second PTFE layer with a pore size of 0.1 microns.

A sensing component 10 may also include a borosilicate sensing element such as those discussed in the U.S. patent application Ser. No. 11/526,393 titled "CARBON DIOXIDE DETECTOR HAVING A BOROSILICATE SUBSTRATE" to Rafael Ostrowski and Martin Debreczeny filed on Sep. 25, 2006, which is hereby incorporated by reference in its entirety herein. An example of a medical device appropriate for use with a borosilicate sensing element is the endotracheal tube 28, depicted in FIG. 2. In this particular embodiment, the endotracheal tube 28 includes multiple borosilicate sensing components 30 disposed along the inside lumen of a conduit 32 adapted to transfer air from the Y-shaped circuit 16, for example into a patient's lungs. The borosilicate sensing components 30 may include a substrate 44 and an indicator solution, discussed in more detail herein.

The borosilicate sensing components 30 are generally adapted to change color in a reversible manner upon exposure to a critical threshold of carbon dioxide. Thus, during a patient respiratory cycle, respiratory gases from the lung enter the endotracheal tube 28 at the distal end and encounter the borosilicate sensing components 30 along the length of the tube. As gas containing expired carbon dioxide flows through the endotracheal tube, each of the borosilicate sensing components 30 in turn will respond to the increased local concentration of carbon dioxide. If the concentration is greater than the critical threshold, a color change will result. As the expired gas flows past each individual borosilicate sensing component 30, after a certain amount of time the color change may reverse as the local carbon dioxide concentration drops around an individual borosilicate-sensing component 30. Thus, the color change may occur as a wave along the endotracheal tube 28. As such, a healthcare practitioner may track expired carbon dioxide in a respiratory gas mixture as it flows along the endotracheal tube 28 or any other airway device during an individual breath.

The borosilicate-sensing components 30 may be any suitable size or shape. In certain embodiments, it may be advantageous for the borosilicate sensing components 30 to be at least large enough to be seen with the naked eye. In other embodiments, the color change may be monitored electronically. The borosilicate sensing components 30 may be spaced at any suitable distance along the endotracheal tube 28. In certain embodiments, the borosilicate-sensing components 30 may be spaced at least 5 mm apart, at least 1 cm apart, or at least 10 cm apart. As the borosilicate sensing-components 30 in the intubated portion of the endotracheal tube may not be visible to a healthcare worker, it may be advantageous in certain embodiments to couple the borosilicate-sensing components 30 to an optical sensor that is able to detect the indicator solution color change and provide a related electrical signal. The optical sensor may be coupled to the monitor 11 such that the electrical signal may be further processed. In certain embodiments (not shown) the borosilicate-sensing components 30 may be disposed on the breathing circuit 12. In such an embodiment, a visual color change may provide information to a healthcare worker about the flow of carbon dioxide through the breathing circuit 12. However, it should be understood that the borosilicate sensing components 30 in such an embodiment may also include optical sensors that provide an electrical signal to the monitor 11.

The substrate 44 may include any borosilicate-containing material. Specifically, it may include borosilicate fibers. These fibers may be produced using any conventional methods, such as melt blowing and spinning. The substrate may include a mesh of borosilicate fibers. More specifically, it may include a thin, highly porous mesh to facilitate rapid infiltration of carbon dioxide gas into the substrate.

The borosilicate-containing substrate 44 may be sufficiently hydrophilic to allow the indicator solution to spread evenly over the substrate 44 and be well absorbed when it is first applied. The indicator solution may then be dried, but still retain sufficient water to allow reaction with carbon dioxide. However, the borosilicate substrate may also not be so hydrophobic that its shelf-life is compromised. The borosilicate-containing material may also include an acrylic binder. In specific embodiments, this binder may be no more than 5% by weight or volume of the total substrate without indicator. Metrigard® membranes containing acrylic binder sold by Pall Corporation (New York) or a similar acrylic binder may be used.

The indicator solution may contain an indicator, such as a chromogenic dye, in a solution. The indicator solution may be coated onto or impregnated into the substrate 44. It may have a surface exposed to or near air or gas within the sensing element 30. The indicator solution may be able to respond rapidly and positively to the presence or absence of certain concentrations of carbon dioxide. More specifically, it may be able to respond to concentrations of carbon dioxide normally present in air respired from a human, such as between approximately 2% and 5% or higher. The indicator solution may also be able to respond to concentrations of carbon dioxide in air respired from a human with perfusion failure, such as concentrations between approximately 0.5% and 2%. Finally, the indicator solution may show no response to carbon dioxide concentrations normally present in external air or esophageal air, such as concentrations below approximately 0.5% and more specifically, concentrations between 0.03% and 0.5%.

Response times to changing carbon dioxide levels in detected air may be between virtually instantaneous to about 20 seconds. Further, a borosilicate substrate 12 may exhibit virtually instantaneous response times of less than 1 second, which is an improvement over typical calorimetric carbon dioxide detection systems. Response may include a calorimetric indication, such as change of the indicator from one color to a very distinct second color. However, once the color begins to change, the change from one color to the other color may be virtually instantaneous as seen by the human eye. In order to attain the above response properties, the indicator in the indicator solution may have a pK lower by 1.0-1.5 pH units than the pH of the indicator solution. This difference allows the indicator solution not to change color instantly when exposed to air, allowing the detector system to be removed from packaging then connected to another device, such as a resuscitator. However, due to a greater resistance to negative effects of air exposure when a borosilicate or borosilicate+acrylic substrate is used as opposed to cellulose filter paper, an indicator pK outside of this range may still be acceptable. In general, any pK sufficient to allow the carbon dioxide detector to remain exposed to room or outside air for at least 15 minutes, at least 30 minutes, at least 60 minutes, or at least 120 minutes without significant color change may be sufficient.

The indicator solution may include an alkaline solution containing hydroxyl ions or amine residues that react chemically with carbon dioxide to form a carbonate and/or a bicarbonate or carbamate moiety. This reaction may be represented by the following equations:

$$CARBON\ DIOXIDE + H_2O \leftrightarrow HCO_3^- + H^+ \qquad I.$$

$$CARBON\ DIOXIDE + H_2O \leftrightarrow CO_3^{2-} + 2H^+ \qquad II.$$

$$CARBON\ DIOXIDE + R_2NH \leftrightarrow R_2NCOO^- + H^+ \qquad III.$$

This reaction depletes the hydroxyl ion or amine at the interface between the indicator solution and air and this lowers the pH at the surface of the indicator solution where it is adjacent or nearly adjacent to air. This depletion results in the diffusion of new base from elsewhere in the indicator solution to its surface to maintain a surface pH similar to that of the indicator solution overall.

More specifically, the concentration of OH⁻ or amine in the bulk of the indicator solution impregnated in or coated on the substrate 44 helps determine the rate of diffusion of base to the surface of the indicator solution. The rate of the chemical reaction at this surface is determined by the nature of each specific reacting species. The rate of reaction at the surface of the indicator solution may be expressed by the equation $R=K_A[\text{CARBON DIOXIDE}][A]$, where [x] represents the concentration of a species in moles/liter and $K_A$ is a constant specific for reactant species A. In a specific embodiment, A is the indicator. The balance of base between the surface and remainder of the indicator solution is also influenced by the contact time between the surface and the gas to which it is exposed, the composition of the substrate 44, which determines the diffusivity constant for A and thus the rate of diffusion of A to the surface, and the concentration of carbon dioxide in the gas, which determines the rate of diffusion of carbon dioxide into or near the surface of the indicator where it may react with the indicator.

The concentration of $OH^-$ or amine in the indicator solution, the rate of the chemical reaction, the contact time between the indicator surface and the gas, and the diffusivity constant for A may all be pre-determined by the manner in which the carbon dioxide detector is constructed and the manner in which it is used. This leaves the concentration of carbon dioxide in the gas the only variable parameter with significant effect, allowing for its measurement.

The concentration of $OH^-$ or amine in the indicator solution and the rate of the chemical reaction may be selected such that the pH near the surface of the indicator solution decreases sufficiently in the presence of a certain concentration of carbon dioxide to cause a color change in the indicator solution. For example, the color change may occur if the concentration of carbon dioxide in the tested air is greater than approximately 2%. This color change may occur within 1 to 20 seconds of exposure of carbon dioxide detector 10 to the air. In a specific example, a concentration of $OH^-$ sufficient to produce a pH of 9.6+/−0.2 in the indicator solution is sufficient to provide this sensitivity.

As noted above, the indicator may have a pK sufficiently lower than the pH of the indicator solution so that a color change does not occur upon exposure to room or outside air for a certain time period. Exposure to air causes the pH at the surface of the indicator solution 14 to gradually decrease, but if such decrease is sufficiently slow, the desired time period without color change limitation may still be met.

The indicator used may affect which base is used to provide an alkaline the indicator solution. For example, if the pK of the indicator is too low, it is possible that with certain bases the pH of the indicator will not drop low enough to cause a color change in the presence of an elevated carbon dioxide concentration. For example, when a sodium hydroxide base is used, the carbonate reaction product is water soluble and also a base. This buffers a pH decrease and may prevent the pH from reaching a level able to trigger a color change in the indicating element if the indicator has a low pK. Calcium hydroxide may be used as a base in embodiments of this description. Calcium hydroxide serves as a source of hydroxyl ions, but its carbonate reaction product with carbon dioxide is insoluble and, therefore, unable to buffer the indicator solution against a decrease in pH. Thus calcium hydroxide may be used with indicators having relatively low pKs, such as metacresol purple rather than, for example, thymol blue or phenol phthalein. This also allows for increased resistance to color change when exposed to room or external air. However, the use of a borosilicate or borosilicate+acrylic in the substrate 44 may allow use of a buffering source of hydroxyl ions in the indicator solution.

Various colorless compounds may be used to provide an alkaline the indicator solution. These include, but are not limited to calcium hydroxide, sodium carbonate, lithium hydroxide, sodium hydroxide, potassium hydroxide, magnesium hydroxide, potassium carbonate, sodium barbitol, tribasic sodium phosphate, dibasic sodium phosphate, potassium acetate, monoethanolamine, diethanolamine, and piperidine. However, if an acrylic-bound borosilicate is used as a substrate, no base may be needed.

Various pH sensitive indicators may also be used in the indicator solution. These include, but are not limited to metacresol purple, thymol blue, cresol red, phenol red, xylenol blue, a 3:1 mixture of cresol red and thymol blue, bromothymol blue, neutral red, phenolphthalein, rosolic acid, α-naphthelphthalein, and orange I. Other pH indicators, the color change that occurs, and the relevant pH as well as other information may be found in the CRC Handbook of Chemistry and Physics, 8-17, 75th Edition 1994.

The indicator solution may also contain a hygroscopic, high-boiling, transparent, colorless, water-miscible liquid. This liquid may entrap sufficient water in the indicator solution when it is coated onto or impregnated into the substrate 44 to allow reaction of the surface of indicator 14 with carbon dioxide present in carbon dioxide detector 10.

Example hygroscopic, high-boiling, transparent, colorless, water-miscible liquids that may be used in the indicator solution include, but are not limited to glycerol, propylene glycol, monoethylene glycol, diethylene glycol, polyethylene glycol, and aliphatic alcohols. In specific embodiments, glycerol and propylene glycol or mixtures thereof may be used because of their antiseptic and non-toxic properties. Acrylic binder used in some embodiments of the disclosure also increases the hydrophobicity of the substrate 44 and may thus decrease the need for a hygroscopic, high-boiling, transparent, colorless, water-miscible liquid in the indicator solution.

The indicator solution may be in an aqueous solution, or it may not be in solution in water. It may require or benefit from the presence of water, or may function independently of water. The indicator solution may also be any type of chromogenic agent. For example, it may be a chromogenic agent that does not go into solution in water, but that nevertheless relies on nearby water.

When used, an acrylic binder provides a more basic environment for an indicator and also increases the hydrophobicity of the substrate. A basic environment may help keep the color of the indicator appropriate in low carbon dioxide situations, such as less than 0.5%. Acrylic is an electron rich compound, which makes it a good Bronstead and Lewis base. The resulting ability to accept protons from proton rich compounds and to donate a pair of electrons to electron poor compounds allows the indicator to remain unreacted. Enough carbonic acid is formed to affect the indicator, but some of the acid is reacted by the acrylic.

A desired ratio of proton acceptance to compound concentration may be determined for different detectors. Varying the concentration of the acrylic binder will have an effect on the amount of carbonic acid available to react with the indicator when carbon dioxide is present in larger amounts. Thus, carbon dioxide detectors 10 that also contain acrylic binder in the substrate 44 may not use sodium carbonate because the binder itself may provide a more basic environment for the indicator. When acrylic binder is used, the final color of dried indicator may also be less sensitive to changes in the pH of the indicator solution. This may allow for a decrease in the amount of indicator in the indicator solution by as much as approximately 66% as compared to cellulose-based carbon dioxide detectors.

In a specific embodiment, the indicator solution may include 0.0169 g of cresol red, 275 mL triethylene glycol, and 725 mL deionized water. This indicator solution may lack carbonate. The indicator solution may be immobilized on the substrate 44 by drying, which removes a substantial amount of water. However, the reaction between the indicator and carbon dioxide may utilize water. Therefore, some water may be absorbed by the indicator solution and/or the substrate 44 before use. For example, water may be absorbed from ambient air. In a specific embodiment, sufficient water may be absorbed in the time period required to remove carbon dioxide detector 10 from protective packaging and begin its actual use. For example, sufficient water may be absorbed by the indicator solution in less than 10, 5 or 1 seconds after the opening of any protective packaging.

The indicator solution may also be placed on the substrate 44 in various other forms or using other methods. For example, it may be provided in a hydrogel. The substrate 44 may also be treated, for example by plasma treatment, prior to administration of the indicator solution.

Use of a borosilicate substrate may result in desirable response time and shelf life of a carbon dioxide detector, while retaining the capacity of the detector to cycle from one color to another quickly from breath to breath. For example, in some carbon dioxide detectors, reaction of the substrate with cresol red, which is used as a color indicator, eventually changes the color indicator irreversibly from purple to yellow. This change makes the detector color insensitive to the presence or absence of carbon dioxide. As a result, the detector system is no longer functional. Although packaging can help prevent this sensor aging, it nevertheless may limit shelf life. Borosilicate substrates do not react with cresol red. As a result, the same shelf life as is obtained with other substrates may be achieved with borosilicate and more cost effective packaging, or, a longer shelf life even in the same packaging may be achieved. In certain embodiments, the shelf life of a borosilicate-based carbon dioxide detector may be greater than 5 years, great than 10 years, or greater than 14 years. Further, while the shelf life of a borosilicate-based carbon dioxide detector may be greatly improved, the packaging employed may be reduced, due to the stability of the borosilicate-based carbon dioxide detector. While other calorimetric carbon dioxide detection systems may employ dessicants to extend their shelf lives, a borosilicate-based carbon dioxide detector may achieve a long shelf life (e.g. several years) without the use of a dessicant.

Additionally, the borosilicate substrate 12 may exhibit an improved color cycling pattern in the presence of carbon dioxide. For example, with use of a common indicator solution 14, such as metacresol purple, the substrate 12 may change from a deep purple to a light tan color, rather than purple to yellow, in the presence of carbon dioxide. One advantage of a purple-to-tan color change rather than a purple-to-yellow color change is that the contrast ratio between purple and tan is particularly advantageous, allowing a healthcare worker to distinguish finer gradations of carbon dioxide levels. Further, the purple-to-tan color change is also helpful for people with color blindness, which most often impairs acuity in the green-yellow-red portion of the spectrum.

The performance of carbon dioxide detectors in humid air is significant to clinical use because exhaled breath contains considerable amounts of water. Thus, performance in humid conditions is indicative of performance with actual patients. It may affect the use-life of a detector. Accordingly, carbon dioxide detectors having a borosilicate and acrylic substrate show faster breath-to-breath response than those having a cellulose fiber substrate such as paper. This faster response is also facilitated by the highly porous nature of borosilicate, which allows easier penetration of air than does a cellulose fiber substrate. This may indicate a longer use-life of the borosilicate substrate detector.

Color indicators may approximately match the color of the indicator solution in the presence of difference levels of carbon dioxide. For example, in one embodiment, a color indicator may reversibly change color from purple to yellow in the presence of sufficient levels of carbon dioxide. In one specific embodiment, a generally yellow color may correspond with normal expiration, while a generally purple color may correspond with normal inspiration. Color indicators may also include written or other visual information to allow a user to determine what carbon dioxide concentrations are indicated by various colors. For example, one portion of borosilicate sensing component 30 may show one or various shades that correlate with a low carbon dioxide concentration, such as below approximately 0.5% or between approximately 0.03% and 0.5%. In such an embodiment, a borosilicate sensing component 30 may contain shades of purple. Another portion of a borosilicate sensing component 30 may show one or various shades that correlate with a high carbon dioxide concentration typical of respired air, such as above approximately 2% or between 2% and 5%. In such an embodiment, the borosilicate-sensing component 30 may contain shades of yellow. An additional portion of a borosilicate-sensing component 30 may indicate carbon dioxide concentrations above that of normal or esophageal air, but below that corresponding with normal respiration. For example, a portion of a borosilicate-sensing component 30 may indicate carbon dioxide concentrations common in respired air of a patient suffering from perfusion failure. A portion of a borosilicate sensing component 30 may show one or various shades that correlate with carbon dioxide concentrations of between approximately 0.5% and 2%. In one specific embodiment, a portion of a borosilicate-sensing component 30 may contain shades of grayish purple. Detection may include in-stream detection, such as in the current EasyCap™ (Nellcor, Tyco Healthcare, California) system. It may also include "side-stream" detection, such as in the current INdCAP™ product (Nellcor, Tyco Healthcare, California). The detection system may be modified to facilitate either form of detection.

Figure 2:
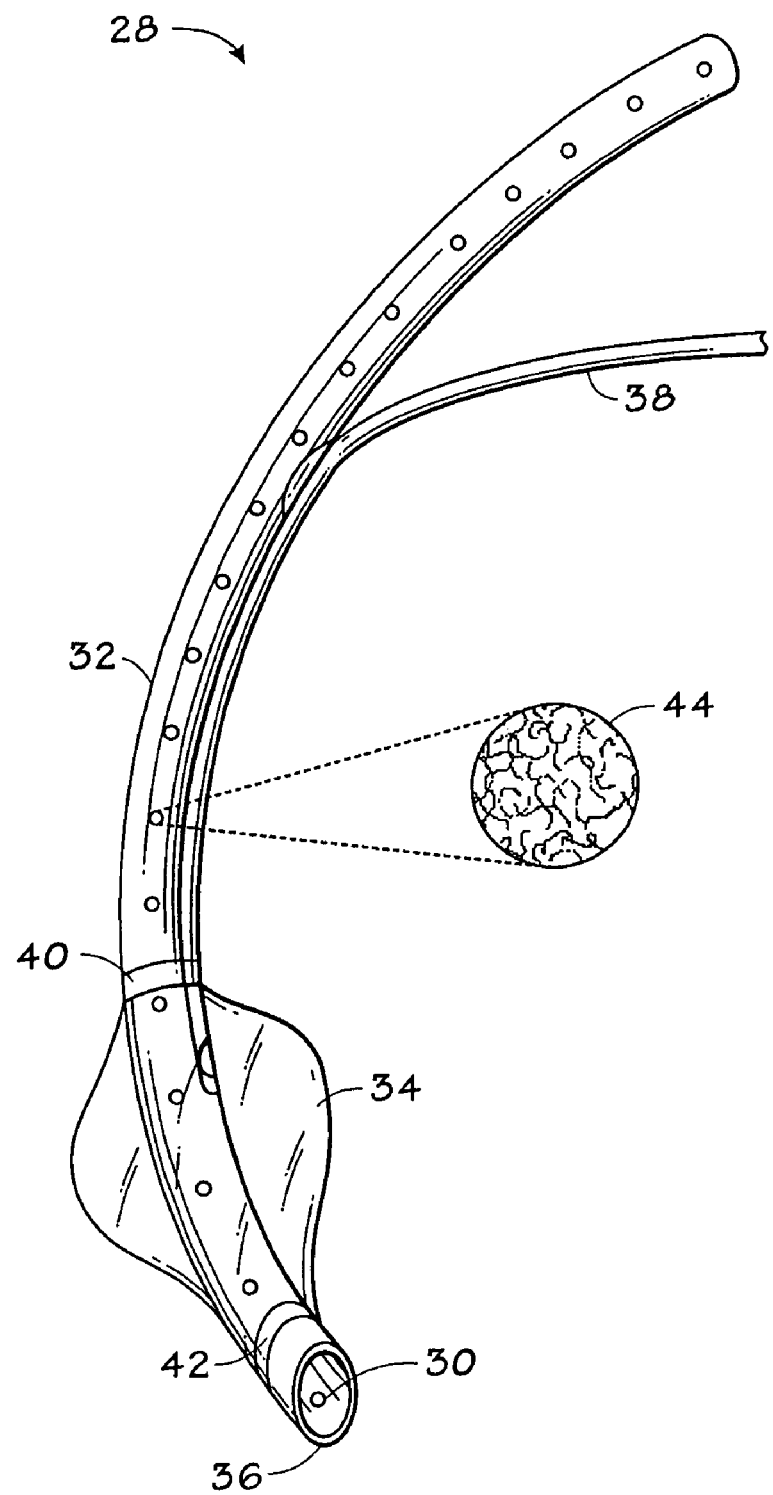
FIG. 2 illustrates an exemplary endotracheal tube with multiple borosilicate carbon dioxide sensing components along the lumen of the tube.

The borosilicate-sensing component 30 may be prepared by forming the substrate 44, then impregnating or coating it with the indicator solution. The substrate 44 may then be dried to immobilize the indicator solution on it. The substrate 44 may then be incorporated into an airway product, as depicted in FIG. 2. During its formation and handling prior to packaging, the borosilicate-sensing component 30 may be kept in conditions to minimize or control chemical reactions that might negatively influence its reliability. For example, it may be kept in dry conditions after drying. Carbon dioxide detectors of the present disclosure may require less stringent pre-packaging conditions than current cellulose filter paper detectors because of improvements in resistance to negative effects of humidity and room air. Carbon dioxide detectors, detection systems, of further systems such as resuscitators may be created in a sterile or clean environment or later sterilized.

The borosilicate-sensing component 30 may be used by exposing it to respiratory gases. The air then infiltrates the substrate 44 and any carbon dioxide in the air reacts with the indicator solution. This may produce a color change in the indicator. Change of color back and forth between a low carbon dioxide color to a high color dioxide color may indicate whether the patient is breathing normally. Change of color to one indicating low concentrations of carbon dioxide still above concentrations in air may indicate perfusion failure in the patient.

Figure 3:
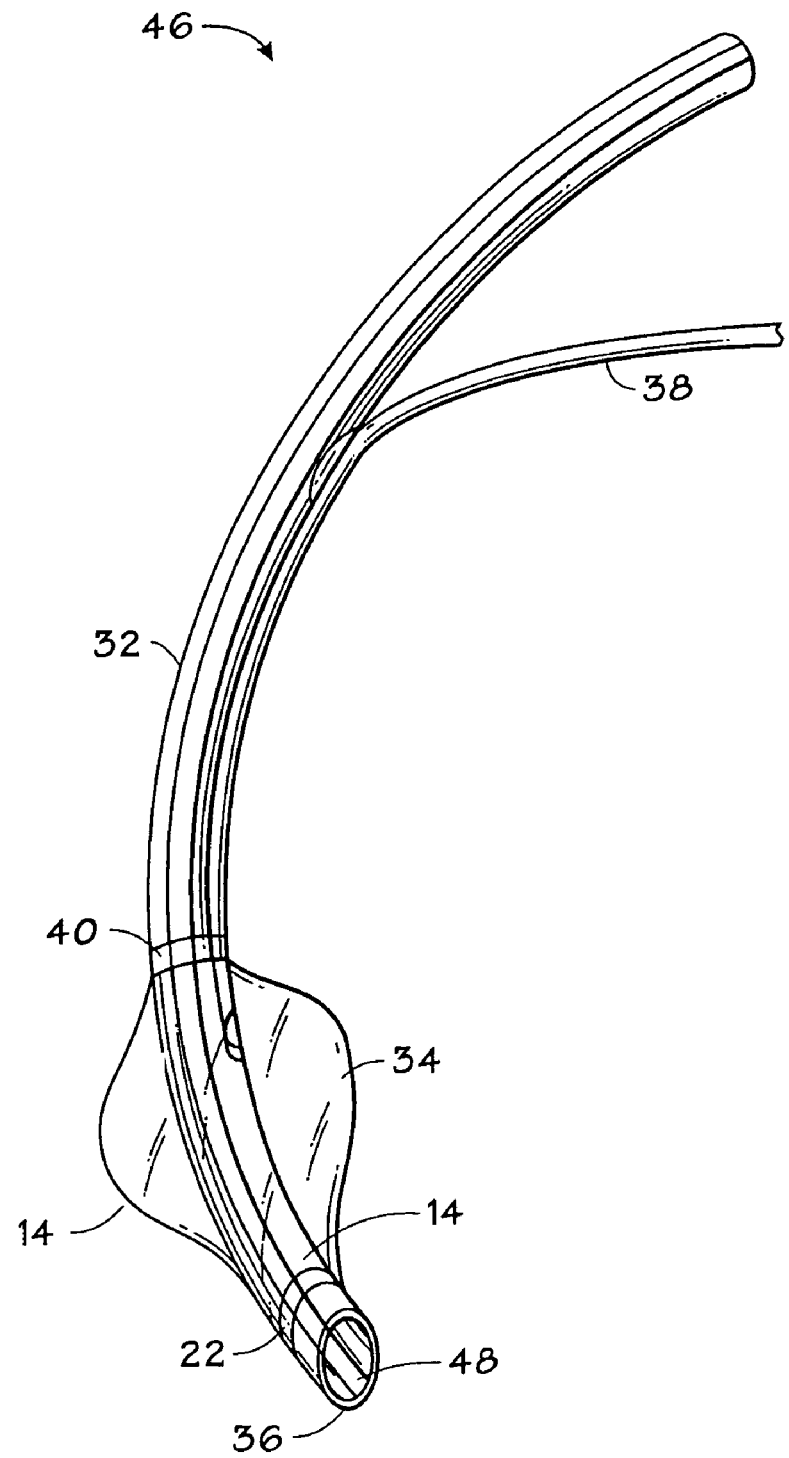
FIG. 3 illustrates an exemplary endotracheal tube with a contiguous borosilicate-sensing component along the lumen of the tube.

In an alternative embodiment, a medical device may include a strip or other contiguous sensing component that provides information about carbon dioxide at a plurality of locations along the device. As depicted in FIG. 3, an endotracheal tube 46 may include a borosilicate-sensing strip 48 that is disposed along the inside passage of the conduit 32. As expired respiratory gases flow through the endotracheal tube 46, the areas of the strip where local concentration of carbon dioxide has reached the critical threshold may change color. As the expired carbon dioxide levels drop after the respiratory gas has moved through the airway, the color change may reverse. Thus, an airway device with a contiguous borosilicate-sensing strip may provide information about carbon dioxide levels at a plurality of locations along a patient breathing circuit.

Figure 4:
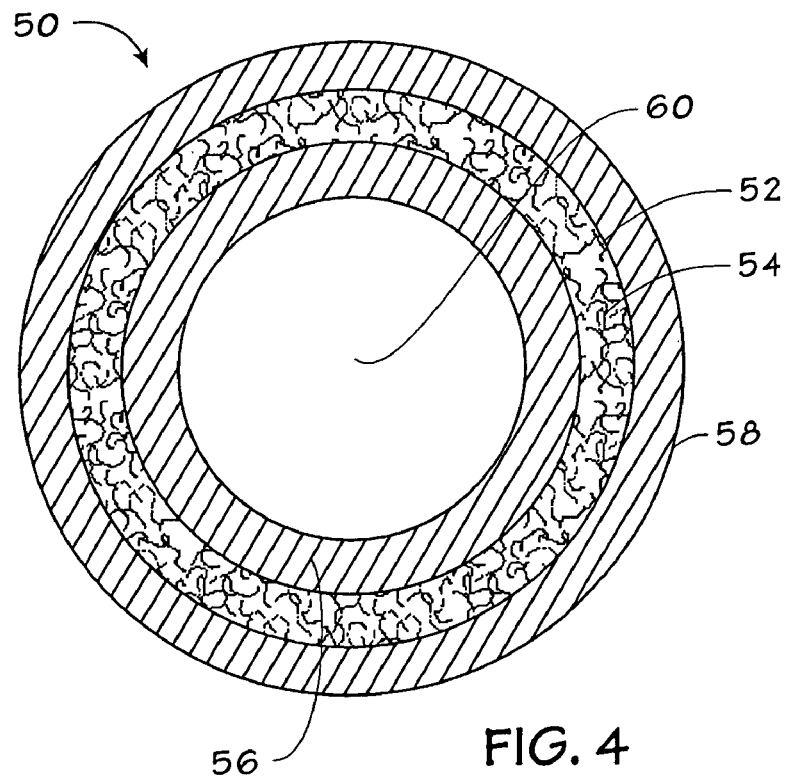
FIG. 4 illustrates a cross-sectional view of an exemplary medical conduit with a borosilicate carbon dioxide sensing layer.

In certain embodiments, a borosilicate-sensing component may be integrated into the material of the airway device itself. For example, FIG. 4 illustrates a cross-sectional view of an exemplary conduit 50 that may be incorporated into a patient breathing circuit. The conduit 50 defines a passageway 60 through which gas may flow. The conduit 50 includes a borosilicate-sensing layer 52 disposed between an inner layer 56 and an outer layer 58. The borosilicate-sensing layer includes borosilicate fibers 54. The inner layer 56 and the outer layer 58 may be extruded over a borosilicate-sensing layer 52. The inner layer 56 may be formed from a material that is relatively permeable to carbon dioxide to allow the carbon dioxide in the passageway 60 to reach the borosilicate-sensing layer 52. The outer layer 58 may be formed from a material that is relatively impermeable to carbon dioxide in order to prevent egress of respiratory gases out of the airway device.

Figure 5:
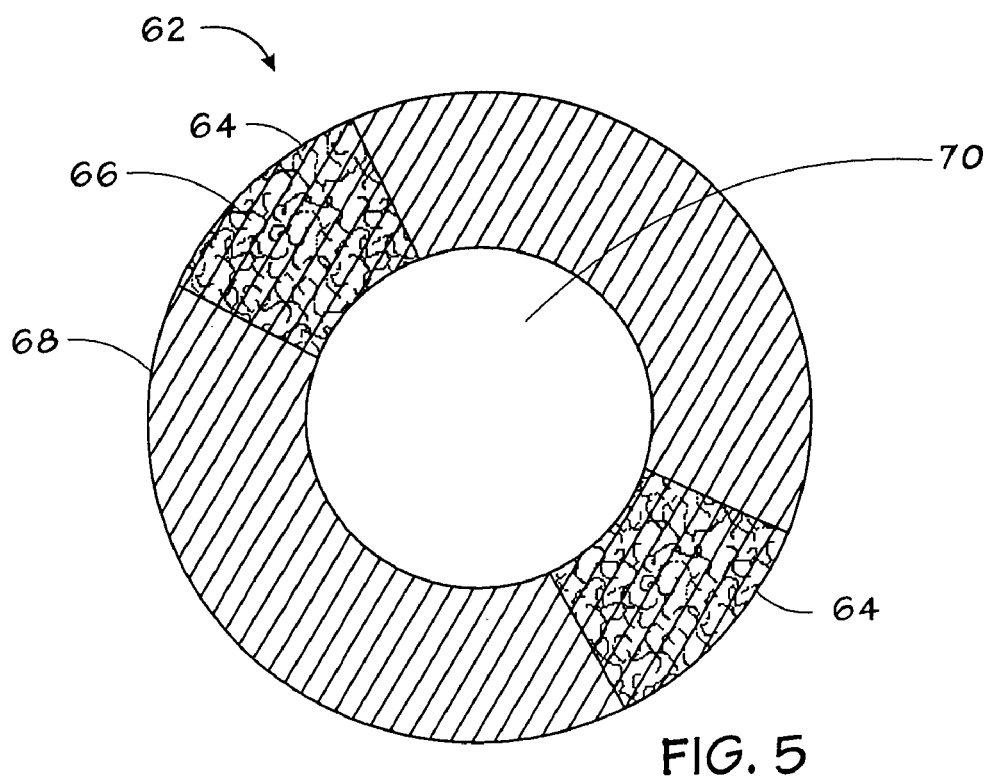
FIG. 5 illustrates a cross-sectional view of an exemplary medical conduit with borosilicate carbon dioxide sensing portions.

FIG. 5 illustrates an alternative embodiment of a conduit 62 that includes at least one embedded borosilicate-sensing portion 64 in a medical tubing structure 68. The borosilicate portion 64 includes borosilicate fibers 66. The conduit 62 defines a passageway 70. Depicted are two borosilicate-sensing portions 64 that may provide the advantage of a time-variable response. As the carbon dioxide in expired respiratory gas moves from the passageway through the sensing portions 64, the indicator response time will be faster for areas of the sensing portions 64 adjacent to the passageway 70 and will be slower for areas of the sensing portions 64 closer to the outside of the conduit 62. Thus, the depth of the sensing portion 64 along the axis orthogonal to the axis of the passageway 70 may slow down the response time of the indicator. In certain embodiments (not shown), the sensing portions 64 may be sealed on the outside of the conduit 62 with a carbon dioxide barrier to prevent egress of respiratory gases to the environment.

Figure 6:
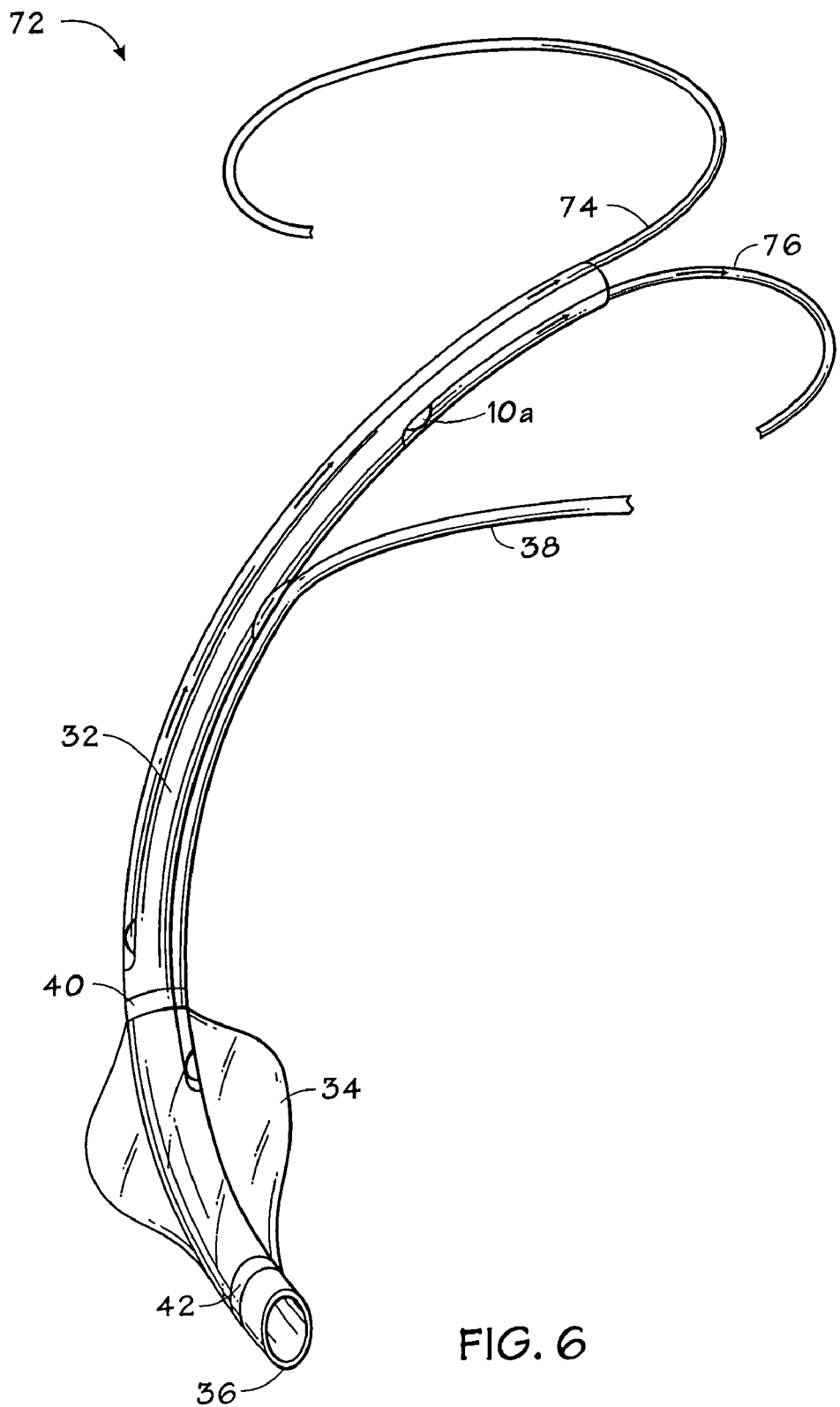
FIG. 6 illustrates an exemplary endotracheal tube with multiple side-sample lumens according to the present techniques.

In an alternative embodiment, an endotracheal tube may be modified to allow for side sampling of respiratory gases at multiple locations along the tube. As depicted in FIG. 6, an endotracheal tube 72 may include a first sampling lumen 74 located relatively closer to a distal end 36 than a second sampling lumen. In such an embodiment, respiratory gases are drawn into the sampling lumen and transferred to a distally located carbon dioxide sensing component. In other embodiments (not shown) a patient breathing circuit may include side sampling lumens at any suitable location. Such an embodiment may be advantageous as a distally located sensing component 10 may be easily replaced while the medical device is still inserted into the patient.

Figure 7:
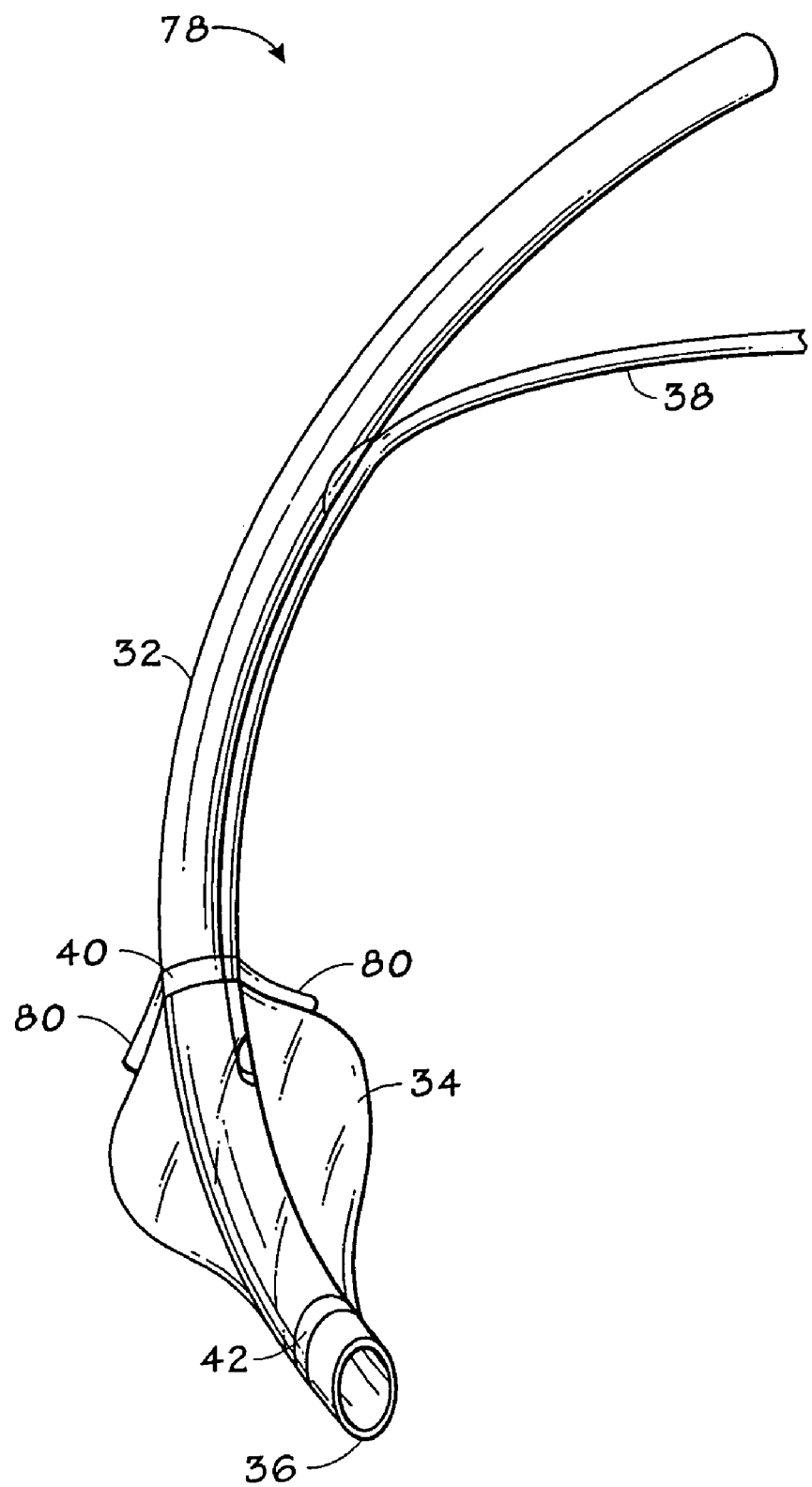
FIG. 7 illustrates an exemplary endotracheal tube with a contiguous carbon dioxide sensing component on the top of the inflatable cuff.

In certain embodiments, carbon dioxide levels may be affected by the buildup of oral-mucosal secretions, either in a conduit through which respiratory gases flow or on the outside of a device after it has been inserted into a patient. As depicted in FIG. 7, an endotracheal tube 78 may include carbon dioxide sensing elements 80 disposed adjacent to a proximal end of a cuff 34. The carbon dioxide sensing elements 80 may provide feedback to a monitor 11 when secretions build up on top of the cuff 34. In such an embodiment, the carbon dioxide sensing elements may facilitate detection of a baseline level of carbon dioxide directly after insertion of the endotracheal tube 78. The baseline level of carbon dioxide may represent a state in which minimal secretions are present. As secretions build up, the carbon dioxide sensing elements 80 may be substantially covered by the secretions, and the measured carbon dioxide levels will typically decrease in response to the presence of the secretions. In certain embodiments, a monitor 11 may provide feedback to a healthcare practitioner to indicate that secretions should be aspirated from the cuff in response to the signal received from the carbon dioxide sensing elements 80. Further, such aspiration may be triggered as an automated response to the decrease of detection of ambient carbon dioxide by the cuff.

In an alternative embodiment (not shown) a sensing component 10 may be disposed on the inside of the endotracheal tube. In such an embodiment, a monitor 11 may include code operable to detect secretions by evaluating the spatial heterogeneity (variability) of carbon dioxide concentration between multiple carbon dioxide sensing components 10 disposed inside the endotracheal tube, at multiple spots along the length of the tube and/or multiple angles inside its circumference. Further, the monitor 11 may provide an indication to the clinician to suction secretions from the ET tube when it detects them, or the monitor 11 may automatically initiate suctioning. Such a system may include fault-tolerant features that, automatically or with user input, may optionally disregard the signal from one or more of the plurality of sensing components 10, for example if the secretions cannot be easily be removed from that spot, so as to continue to provide reliable secretion detection with a minimum of false alarms.

Figure 8:
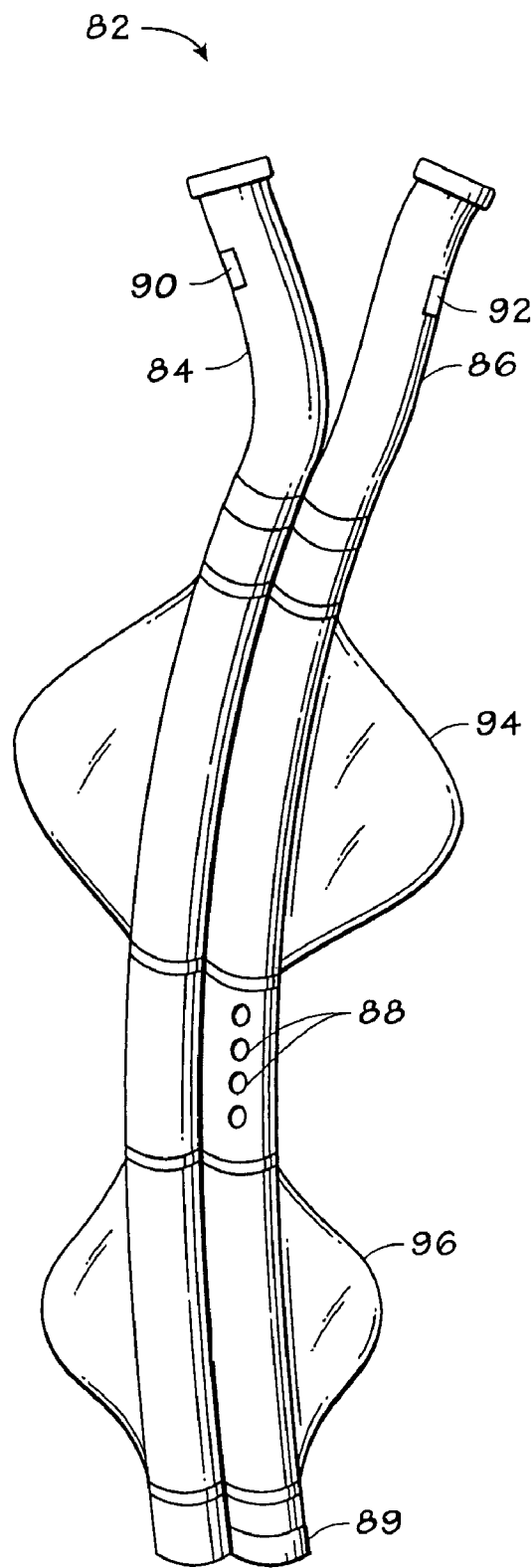
FIG. 8 illustrates Combitube with a carbon dioxide sensing component in the tracheal lumen and the esophageal lumen.

In certain situations, emergency healthcare workers may intubate patients in the field. Often, tracheal intubation is impractical in these situations because of certain time pressures as well as the level of skill associated with tracheal intubation. As a result, emergency healthcare workers often use an esophageal tracheal airway device, such as a Combitube® (available from Mallinckrodt, Pleasanton, Calif.), for emergency intubation. An esophageal tracheal airway device is adapted to enter either the esophagus or the trachea, allowing ventilation and oxygenation in both positions. Depicted in FIG. 8 is an improved esophageal tracheal airway device 82 with carbon dioxide sensing elements 90 and 92 that provide immediate feedback as to which lumen of the dual-lumen esophageal tracheal airway device 82 is active. As depicted in FIG. 8, an esophageal tracheal airway device 82 generally includes a tracheal lumen 84 and an esophageal lumen 86 with a distal blocked end 89 and perforations 88 at the pharyngeal level. The esophageal tracheal airway device 82 may also include an oropharyngeal balloon 94 and a smaller balloon 96 in order to substantially seal the patient airway. Once the esophageal tracheal airway device 82 has been inserted into a patient, a healthcare worker may determine whether the esophageal tracheal airway device 82 entered the trachea or the esophagus by determining which lumen is active. For example, if carbon dioxide sensing element 90 provides a visual indication of carbon dioxide flow, a healthcare worker will know that the esophageal tracheal airway device 82 was inserted into the trachea. Similarly, a positive carbon dioxide visual signal from carbon dioxide sensing element 92 indicates that the esophageal lumen 86 is active.

In an alternative embodiment (not shown), a carbon dioxide sensing element 10 may be incorporated into each of the dual lumens of a breathing circuit designed for independent ventilation of one or both of a patient's two lungs. In this case, having a carbon dioxide sensing element 10 on each individual lumen that is specific to an individual lung would provide the advantage of enabling capnography for each lung, including estimation of dead space and changes therein for each lung. For example, independent lung ventilation may be advantageous if the patient has a lung tumor, as surgeons may ventilate one lung while excising a tumor on the other. In other embodiments, damage to an individual lung may result in independent ventilation of each lung at different pressures. In certain embodiments each lumen may include a borosilicate sensing strip operatively connected to a monitor 11.

In certain embodiments, it may be advantageous to employ the techniques provided herein for capnography or volumetric capnography, which may provide information about carbon dioxide production, pulmonary perfusion, alveolar ventilation, respiratory patterns and elimination of carbon dioxide from the anaesthesia circuit and ventilator. Typically, capnography involves measuring expiratory gas carbon dioxide concentration against time during multiple respiratory cycles. The carbon dioxide levels measured by the present techniques may produce a graphical capnogram that may illustrate three phases in breath carbon dioxide gas concentration during the patient exhale cycle in a healthy patient. The first phase indicates clearing of the conducting airways which do not normally participate in gas exchange and which are referred to as "dead space." The second phase typically involves exhalation of air from conducting airways dynamically mixed with lung gases from the active (alveoli) membrane surfaces within the lung that have undergone gas exchange with arterial blood. The third phase reflects the exhalation of unmixed gas from regions of the lung that are normally in active exchange with the alveoli tissue.

Carbon dioxide concentration, when plotted against expired volume during a respiratory cycle, is termed as volumetric canography. The volume of carbon dioxide exhaled per breath can be assessed. A volume capnogram provides information about a variety of clinical states and may enhance the information provided by a time capnogram. For example, a volume capnogram may provide information about physiological dead space. Total "physiologic dead space" can therefore be measured using arterial carbon dioxide and the Bohr equation. "Anatomic dead space," which may include gas volume within a breathing circuit in which exhaled gas is rebreathed, such as the endotracheal tube, passive humidification device, or Y-piece, can be calculated directly from the volume capnogram. Alveolar dead space is the difference between physiologic dead space and anatomic dead space, and is related to the difference between alveolar and arterial carbon dioxide. An increase in physiologic dead space may indicate that the patient is at risk for pulmonary embolism or pulmonary edema.

The present techniques may be employed in volumetric capnography. For example, delays between carbon dioxide changes detected by the sensing elements 10 in breathing circuit 12 could be used, during periods in the breathing cycle when carbon dioxide is changing, to determine the velocity of the gas. Such a calculation may also include inputting the distance between the individual sensing elements 10. Gas flow through the breathing circuit 12 may be calculated by multiplying the velocity by the circuit cross-sectional area. Gas volume is calculated by integrating flow over time. Anatomic dead space may be estimated as the total volume exhaled while carbon dioxide is increasing at the start of exhalation. This method is advantageous in that it does not require a separate flow sensor for this volumetric estimate.

Figure 9:
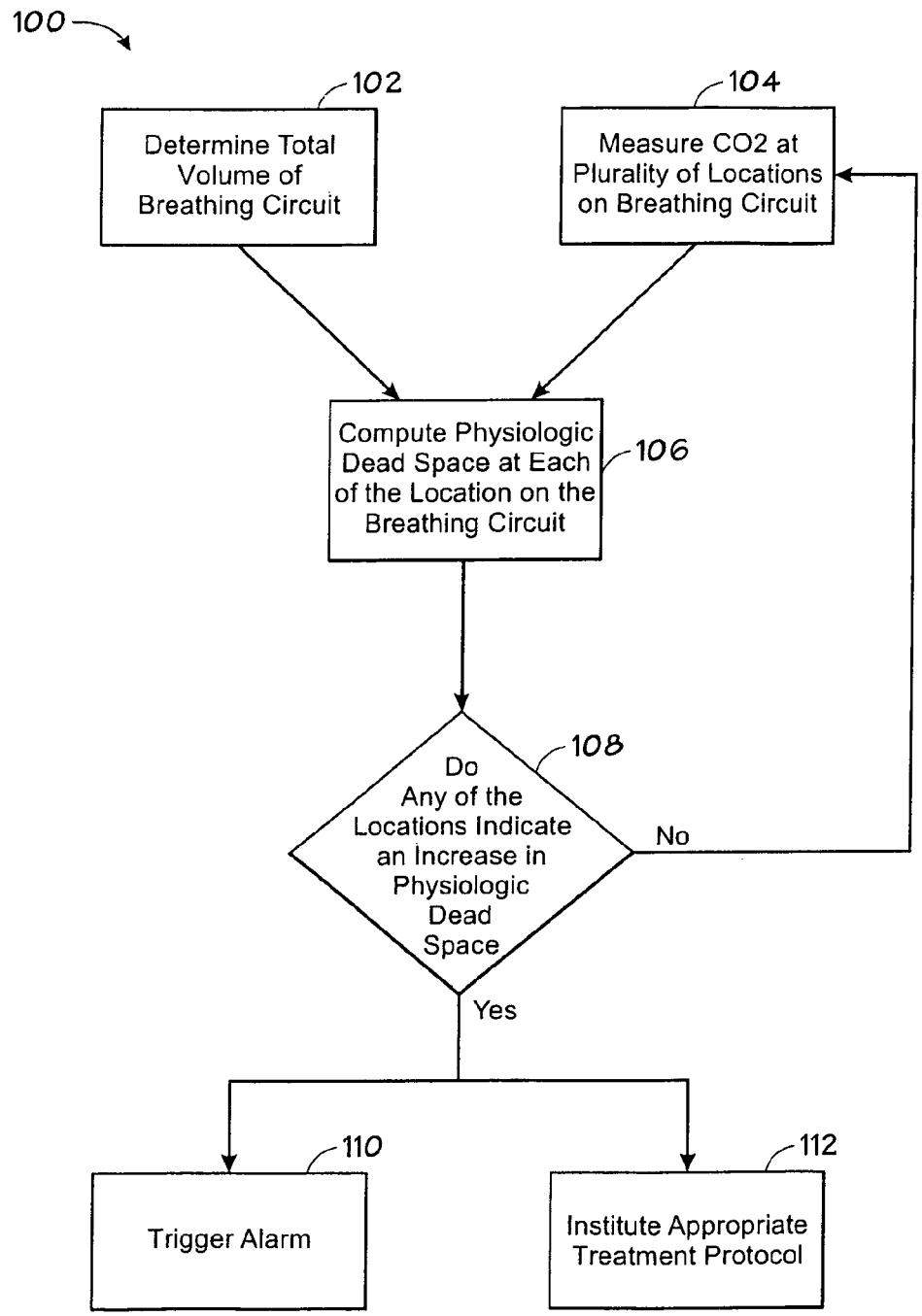
FIG. 9 is a flowchart for determining the physiological dead volume using an endotracheal tube or breathing circuit according to the present techniques.

The flow chart 100 depicted in FIG. 9 describes steps involved in monitoring physiologic dead space, which involves acquisition of tissue carbon dioxide data from the sensing elements 10 at step 104, and the acquisition of total breathing circuit volume data at step 102. In certain embodiments, it is envisioned that steps 102 and 104 may occur simultaneously. In other embodiments, step 102 may be performed by selecting a predetermined setting on a monitor. For example, certain types of medical devices may be associated with a predetermined total volume. The total volume of the respiratory circuit may be determined by multiplying the tube's, for example an endotracheal tube as well as its associated connecting tubing, cross-sectional area by its length. One or more of these dimensions may be input by the user, or they may be estimated from other available information, such as patient weight. Alternatively, the volume of one or more circuit elements may be predetermined at the time of manufacture and stored in a memory device embedded within the respiratory circuit 12 that may then be read by the monitor 11. At a step 106, a processor analyzes the carbon dioxide data and total volume data to calculate physiologic dead space at each sensing element 10 location.

If the volume capnogram at any individual location indicates an increase in physiologic dead space, control is passed to step 110, which triggers an alarm, which may be a visual or audio alarm, and to step 112, which dictates that appropriate treatment protocols are instituted. For example, as physiologic dead space increases may be associated with pulmonary embolism, an appropriate treatment protocol may include administration of anticoagulants. In other embodiments, physiologic dead space increases may be associated with respiratory events such as acute respiratory distress syndrome, shock, sepsis, pneumonia, aspiration asthma attacks, lung injury, or lung collapse. Such events may correlate with particular clinical patterns, which may include progressive hypoxemia, decreased lung compliance, intrapulmonary shunting, and non-cardiogenic pulmonary edema. Particular clinical patterns may be differentiated from one another by patient history and also by unique features of the volumetric capnograms. If, at a step 108, the individual carbon dioxide sensing elements 10 do not indicate any increase in physiologic dead space, a processor passes control back to step 104.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of carbon dioxide, but these techniques may also be utilized for the measurement and/or analysis of other respiratory gases. Rather, the invention is to cover all modifications, equivalents, and alternatives falling within the spirit and scope of the invention as defined by the following appended claims. It will be appreciated by those working in the art that sensors fabricated using the presently disclosed and claimed techniques may be used in a wide variety of contexts. That is, while the invention has primarily been described in conjunction with the measurement of carbon dioxide concentration in the airway, the airways products fabricated using the present method may be used to evaluate any number of sample types in a variety of industries, including fermentation technology, cell culture, and other biotechnology applications.

What is claimed is:

1. An endotracheal tube comprising:
a conduit adapted to transfer gas to or from a patient's lungs;
an inflatable balloon cuff disposed on the conduit, the inflatable balloon cuff having a proximal end, a distal end, and a body extending from the proximal end to the distal end, wherein the inflatable balloon cuff is adapted to form a seal against a patient's tracheal walls; and
at least one carbon dioxide sensing component disposed on the proximal end of the inflatable balloon cuff that does not form part of the seal, wherein the carbon dioxide sensing component is configured to send a signal that correlates to a level of secretions on the cuff.

2. The endotracheal tube of claim 1, comprising a ventilator to which the conduit is operatively connected.

3. The endotracheal tube of claim 1, comprising a selective barrier disposed on at least one sensing component that is substantially impermeable to water.

4. The endotracheal tube of claim 1, wherein the carbon dioxide sensing component comprises a chemical indicator.

5. The endotracheal tube of claim 1, wherein the carbon dioxide sensing component comprises an electrochemical transducer.

6. The endotracheal tube of claim 1, wherein the carbon dioxide sensing component comprises a non-optical transducer.

7. The endotracheal tube of claim 1, wherein the carbon dioxide sensing component comprises an optical transducer.

8. The endotracheal tube of claim 1, wherein the carbon dioxide sensing component comprises a quantum-restricted element.

9. The endotracheal tube of claim 1, wherein the carbon dioxide sensing component comprises a borosilicate substrate; and
a carbon dioxide responsive indicator solution disposed on the borosilicate substrate.

10. The endotracheal tube of claim 9, wherein the borosilicate substrate comprises an acrylic binder.

11. The endotracheal tube of claim 1, wherein the conduit comprises at least one lumen adapted to transfer gas to at least one sensing component.

12. A system comprising:
a conduit adapted to transfer gas to or from a patient's lungs;
an inflatable balloon cuff disposed on the conduit, the inflatable balloon cuff having a proximal end, a distal end, and a body extending from the proximal end to the distal end wherein the inflatable balloon cuff is adapted to form a seal against a patient's tracheal walls; and
at least one carbon dioxide sensing component disposed on the proximal end of the inflatable balloon cuff that does not contact the tracheal walls when the inflatable balloon cuff is inflated, wherein the at least one carbon dioxide sensing component is configured to send a signal that correlates to a level of secretions on the cuff; and
a monitor adapted to be operatively coupled to the at least one carbon dioxide sensing component.

13. The system of claim 12, comprising a ventilator to which the conduit is operatively connected.

14. The system of claim 12, comprising a selective barrier disposed on at least one sensing component that is substantially impermeable to water.

15. The system of claim 12, wherein the carbon dioxide sensing component comprises a chemical indicator.

16. The system of claim 12, wherein the carbon dioxide sensing component comprises an electrochemical transducer.

17. The system of claim 12, wherein the carbon dioxide sensing component comprises a non-optical transducer.

18. The system of claim 12, wherein the carbon dioxide sensing component comprises an optical transducer.

19. The system of claim 12, wherein the carbon dioxide sensing component comprises a quantum-restricted element.

20. The system of claim 12, wherein the carbon dioxide sensing component comprises a borosilicate substrate; and
a carbon dioxide responsive indicator solution disposed on the borosilicate substrate.

21. The system of claim 20, wherein the borosilicate substrate comprises an acrylic binder.

22. The system of claim 12, wherein the conduit comprises at least one lumen adapted to transfer gas to at least one of a plurality of sensing component.

23. A method comprising:
providing a conduit adapted to transfer a gas to or from a patient;
providing an inflatable balloon cuff disposed on the conduit, the inflatable balloon cuff having a proximal end, a distal end, and a body extending from the proximal end to the distal end wherein the inflatable balloon cuff is adapted to form a seal against a patient's tracheal walls; and
providing at least one carbon dioxide sensing component disposed on a proximal portion of the inflatable balloon cuff that does not form part of the seal, wherein the carbon dioxide sensing component is configured to send a signal that correlates to a level of secretions on the cuff.

24. The method of claim 23, comprising providing a ventilator to which the conduit is operatively connected.

25. The method of claim 23, comprising providing a selective barrier disposed on the sensing component that is substantially impermeable to water.

26. The method of claim 23, wherein providing the sensing component comprises providing a chemical indicator.

27. The method of claim 23, wherein providing the sensing component comprises providing an electrochemical transducer.

28. The method of claim 23, wherein providing the sensing component comprises providing a non-optical transducer.

29. The method of claim 23, wherein providing the sensing component comprises providing an optical transducer.

30. The method of claim 23, wherein providing the sensing component comprises providing a quantum-restricted element.

31. The method of claim 23, wherein providing the sensing component comprises providing an elongate borosilicate substrate; and
providing a carbon dioxide responsive indicator solution disposed on the elongate borosilicate substrate.

32. The method of claim 31, wherein providing the elongate borosilicate substrate comprises providing an acrylic binder.

33. The method of claim 23, wherein providing the sensing component comprises embedding the sensing component in the inflatable balloon cuff.

34. A method comprising:
receiving a signal from at least one carbon dioxide sensing component disposed on an inflatable balloon cuff having a proximal end, a distal end, and a body extending from the proximal end to the distal end and wherein the inflatable balloon cuff is operatively connected to an endotracheal tube, and wherein the carbon dioxide sensing component is disposed on the proximal end of the inflatable balloon cuff not in contact with a patient's tracheal walls; and
correlating the signal to a level of secretions on the cuff.

35. The method of claim 34, comprising correlating a decrease in sensed carbon dioxide to an increase in secretions on the cuff.

36. The method of claim 34, comprising comparing the signal to a control.

37. The method of claim 34, comprising activating a visual or audio message if the level of secretions is above a threshold level.

38. The method of claim 34, comprising activating an aspiration assembly if the level of secretions is above a threshold level.

39. A method comprising:
receiving a first signal from a first carbon dioxide sensing component disposed on an endotracheal tube;
receiving a second signal from a second carbon dioxide sensing component disposed on an inflatable balloon cuff associated with the endotracheal tube, wherein the inflatable balloon cuff comprises a proximal end, a distal end, and a body extending from the proximal end to the distal end and wherein the second carbon dioxide sensing component is disposed on the proximal end of the inflatable balloon cuff; and
correlating a difference between the first signal and the second signal to a level of secretions on a surface of the endotracheal tube.

40. The method of claim 39, comprising correlating a decrease in sensed carbon dioxide at the first carbon dioxide sensing component to an increase in secretions on the cuff.

41. The method of claim 39, comprising comparing the signal to a control.

42. The method of claim 39, comprising activating a visual or audio message if the level of secretions is above a threshold level.

* * * * *